(12) United States Patent
Mastors et al.

(10) Patent No.: US 8,807,376 B1
(45) Date of Patent: Aug. 19, 2014

(54) CONTAINER FOR HOSPITAL PATIENTS

(76) Inventors: Patricia M. Mastors, Exeter, RI (US); Joseph C. Cacciola, Wrentham, MA (US); Dana Chicca, Swansea, MA (US)

( * ) Notice: Subject to any disclaimer, the term of this patent is extended or adjusted under 35 U.S.C. 154(b) by 589 days.

(21) Appl. No.: 13/068,703

(22) Filed: May 18, 2011

Related U.S. Application Data

(60) Provisional application No. 61/367,029, filed on Jul. 23, 2010.

(51) Int. Cl.
*A47K 5/08* (2006.01)

(52) U.S. Cl.
USPC .......................................... 220/481; 220/751

(58) Field of Classification Search
CPC .. A47K 3/001; A47K 10/185; A01G 12/0237
USPC ............. 220/7, 481, 476, 751; 206/348, 464; 312/248; 383/23
See application file for complete search history.

(56) References Cited

U.S. PATENT DOCUMENTS

| | | | | |
|---|---|---|---|---|
| 4,858,867 A | * | 8/1989 | King | 248/214 |
| 7,004,629 B2 | * | 2/2006 | Shrader et al. | 383/23 |
| 2005/0258204 A1 | * | 11/2005 | Evans et al. | 224/197 |

* cited by examiner

*Primary Examiner* — Steven A. Reynolds
*Assistant Examiner* — King M Chu
(74) *Attorney, Agent, or Firm* — Robert J Doherty

(57) ABSTRACT

An organizing and storage container especially constructed for use by medical facility patients in which they may store personal items adjacent to their beds, chairs, etc. wherein the container is mounted to such bed, chair, etc. in an elevated position and is free to assume a horizontal position irrespective of the position of the bed, chair and which container is specifically constructed to both protect the contents from bacterial infection but to remind the patient of the continued need to do so.

23 Claims, 26 Drawing Sheets

CONTAINER FOR HOSPITAL PATIENTS

This application claims the benefits of U.S. Provisional Patent Application No. 61/367,029 filed May 20, 2010.

BACKGROUND OF THE INVENTION

This application is directed to the safe, convenient and readily accessible storage of personal items of those individuals confined to a hospital setting. Generally when a person is temporarily admitted to a hospital or other medical or care related facility, no provision is made for the convenient storage of the patient's necessary personal belongings such as eyeglasses, dental appliances, cell phone and other items enabling the patient to easily communicate with others and maintain a sense of normalcy. Having such items readily accessible to the patient in a hospital, medical, convalescent, or rehabilitation facility at his/her bedside or other related equipment member, e.g., chair or walker, contributes to the patient's well being, safety, comfort, convenience and recovery. Thus, it would be desirable to provide a container for the storage of such items in close proximity to the patient.

In addition, the transmission of germs or bacteria by hospital personnel and/or visitors to the patient's bedside and/or other hospital related equipment member is of concern; and thus, a container that is easily wiped clean and sanitized while housing the patient's selected personal effects would be desirable.

These and other objects of the invention are accomplished by the provision of an organizing and storage system for patients in hospital and related medical facilities having a floor on which a hospital related member is supported comprising, a pouch-like container and means for attaching said container to a clamp in turn adapted for removable attachment to said hospital related member, said container having a back panel upwardly terminating in a relatively rigid top panel, said top panel supporting said means for attaching said container to said clamp, a front panel attached to said back panel so as to form an interior storage space between the front of said back panel and the back of said front panel and accessible via a top opening, and said attachment means accommodating relative rotation between said attachment means and said clamp such that said container is rotatable to a horizontally parallel position with respect to said facility floor.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 12:
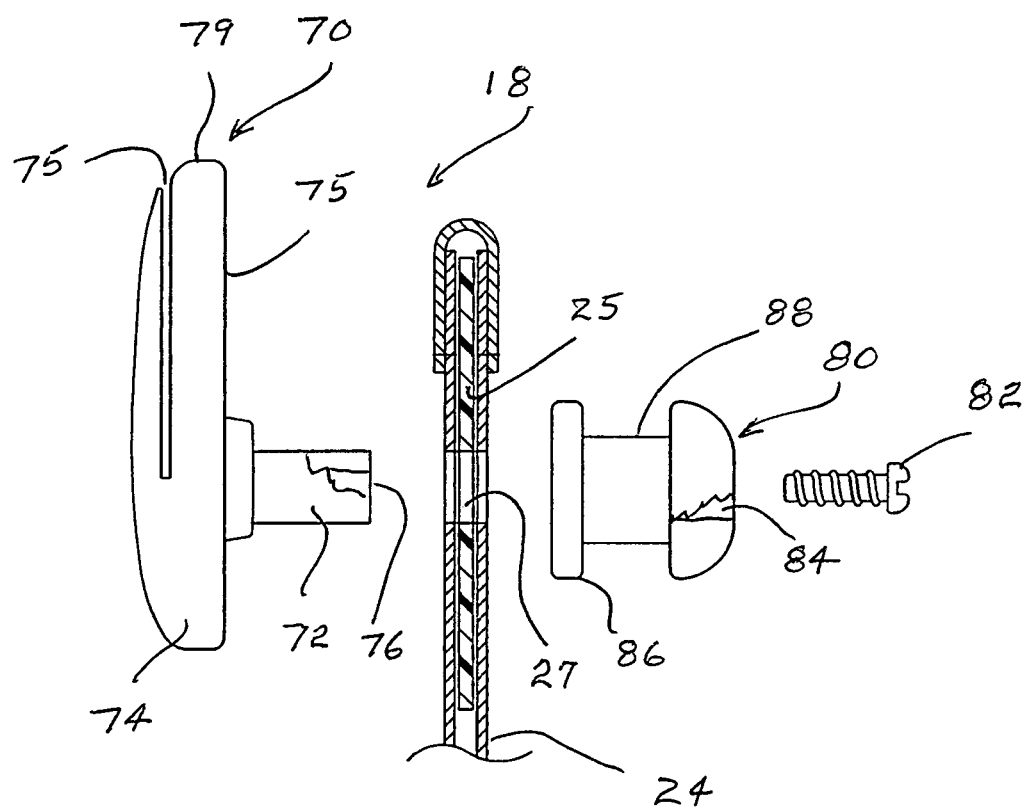
FIG. 12 is an enlarged exploded partial view of one form of the attendant means for attaching the container to the clamp.
Figure 13:
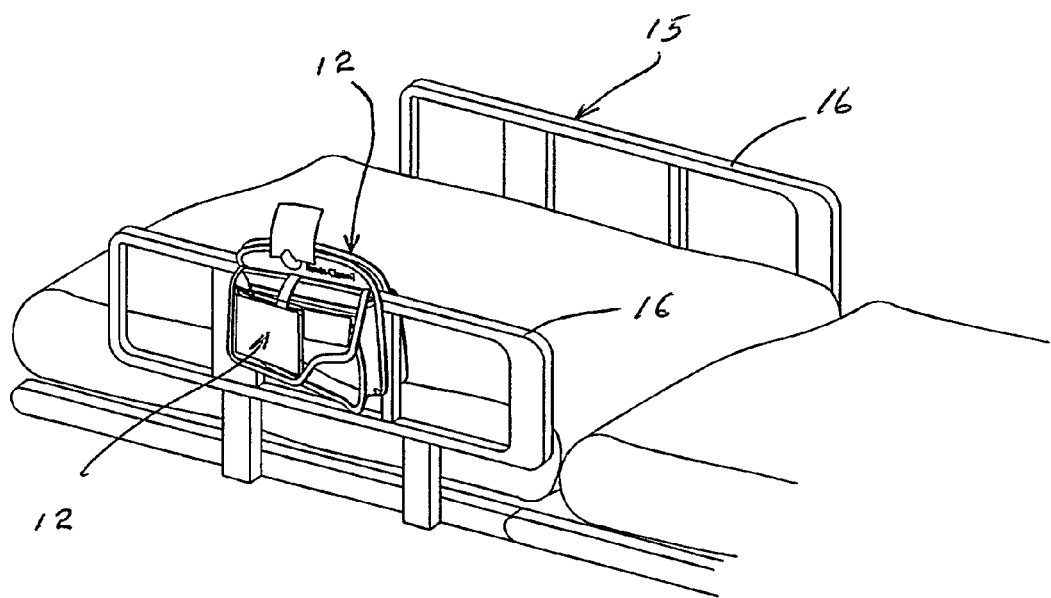
FIG. 13 is a partial perspective view of the container system of the present invention connected to the side rail of a hospital bed and wherein two such containers are supported.

Referring to the drawings and more particularly to FIGS. 1-14, a preferred embodiment of the organizing and storage system 10 of the present invention is shown including a container 12 in which a patient's selected belongings such as eyeglasses, dental devices, cell phone and hand sterilizing lotion may be conveniently stored and positioned in close proximity to the patient. For instance, the container 12 may be mounted to a hospital related member, e.g., one of the side rails 16 of a hospital bed 15 such as depicted in FIGS. 13 and 14, via attachment means 18 such that the container or containers 12 remain disposed in a horizontal position vis-à-vis the floor 20 on which the bed is supported.

Figure 14:
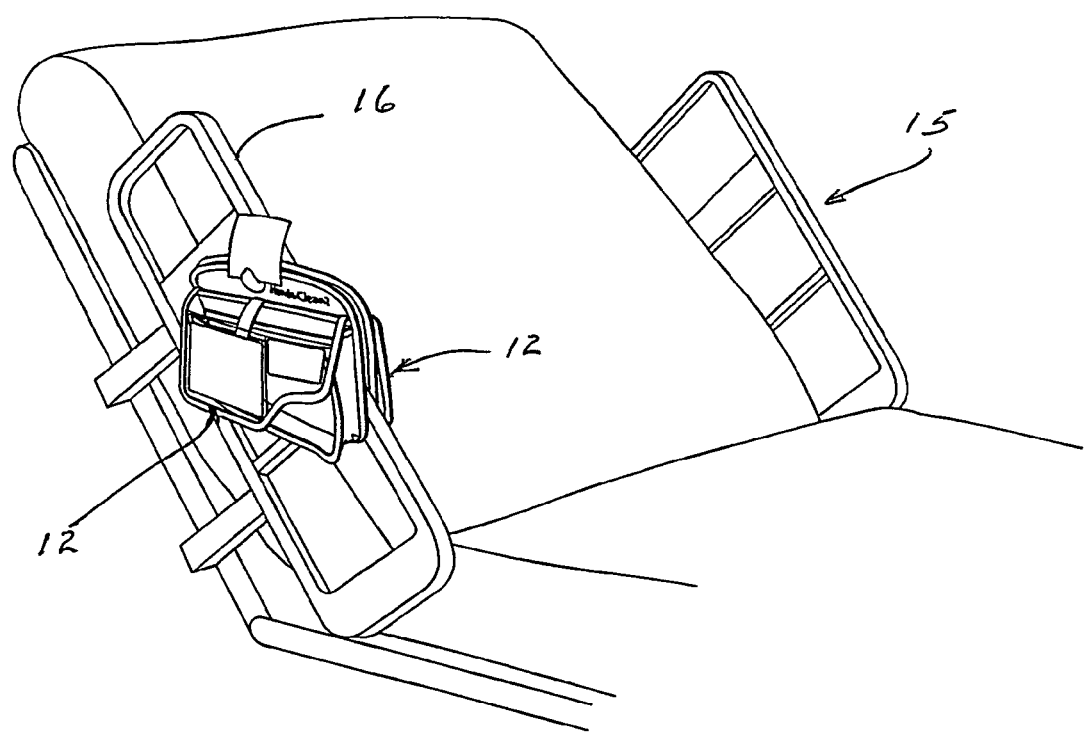
FIG. 14 is a view similar to FIG. 13 but with the bed raised to an elevated position to better illustrate how the containers of the present invention are maintained in a horizontal attitude.

The importance of the container 12 remaining in such horizontal position even when the hospital related member such as the bed side rails are elevated as in FIG. 14 will be more fully apparent as the description continues. One of the primary purposes of the instant invention is that indicia positioned on the container such as messages relating to care, personal identification and reminders will be clearly visible to hospital personnel and/or visitors at all times. In addition, horizontal positioning ensures that personal effects in the container 12 will not be inadvertently spilled or dislodged therefrom irrespective of the movement or positioning of the hospital related member.

The container 12 is essentially of a pouch-like, handbag or soft-sided lunchbox configuration having a back panel 22 which forms the rear of the container and which extends upwardly and terminates in a top panel 24 having an upper edge surface 25 and is preferably an integral continuation of the back panel. A front panel 26 is disposed longitudinally forward of the back or rear panel 22 and is connected thereto via a pair of laterally spaced side panels 28 as well as a bottom panel 30. The side and bottom panels 28, 30 respectively preferably fold upon themselves to provide at least one interior storage space 32 within the container 12 and between the front surface 36 of the rear panel 22 and the rear surface 38 of the front panel 26. In addition, an intermediate panel 39 may be included to provide back-to-back storage spaces 32 and 34.

Figure 1:
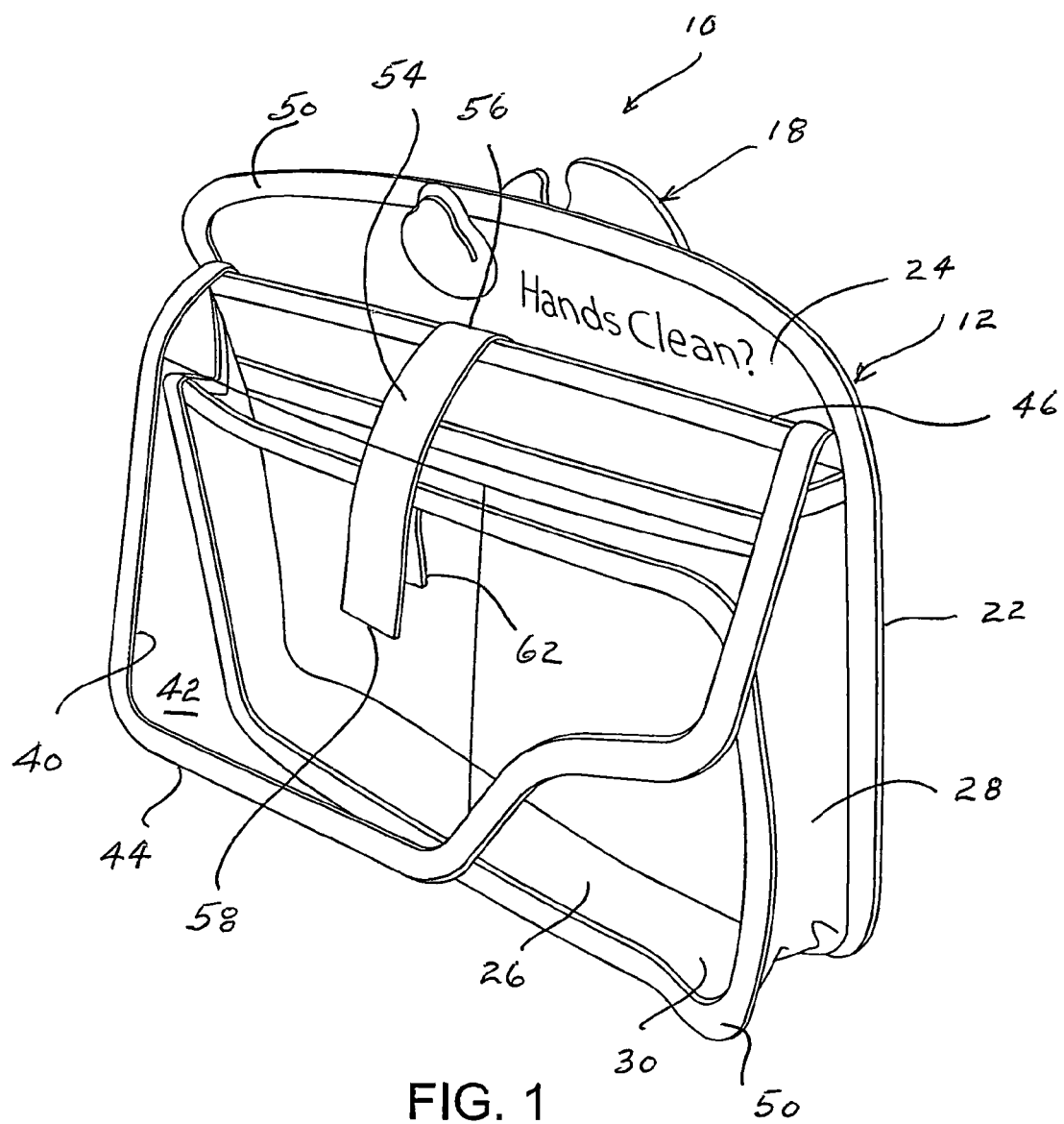
FIG. 1 is a front perspective view of the container system of the present invention in a fully closed position.
Figure 2:
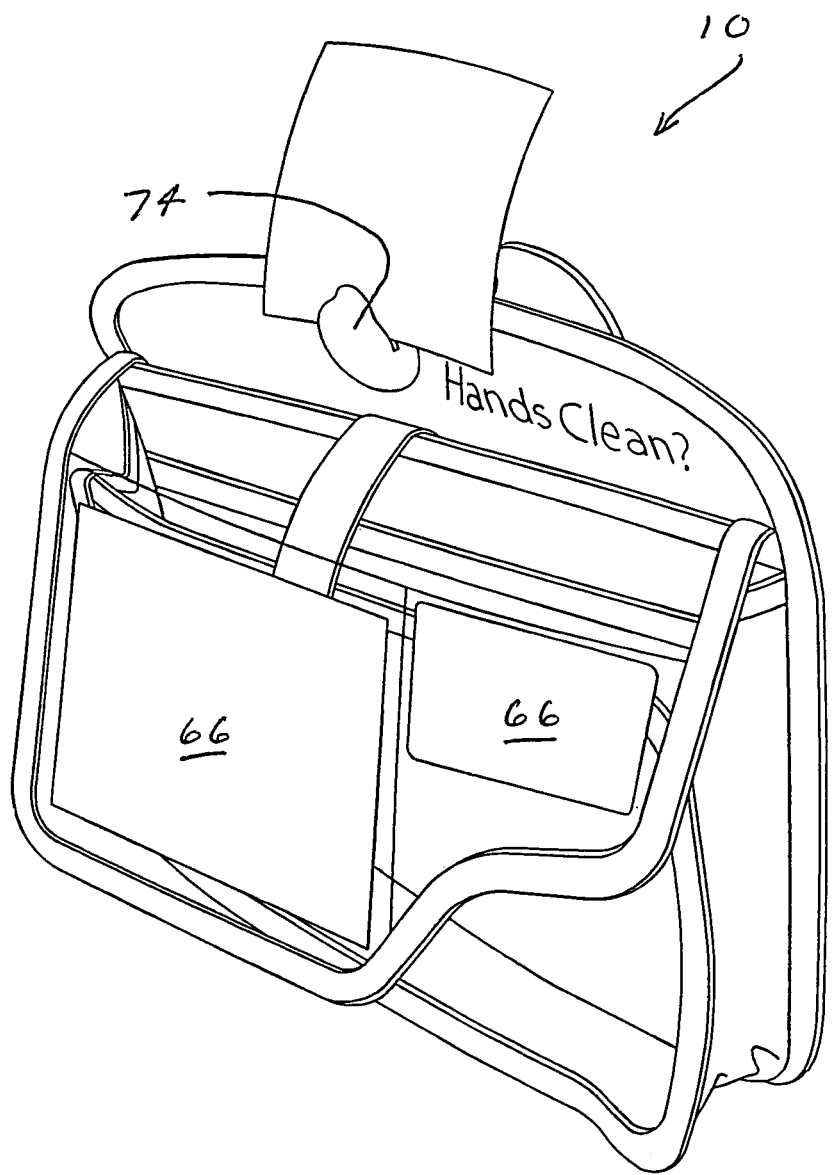
FIG. 2 is a front perspective view similar to FIG. 1 with privacy screens inserted in the container as well as a greeting and/or reminder message displayed at a top portion thereof.
Figure 3:
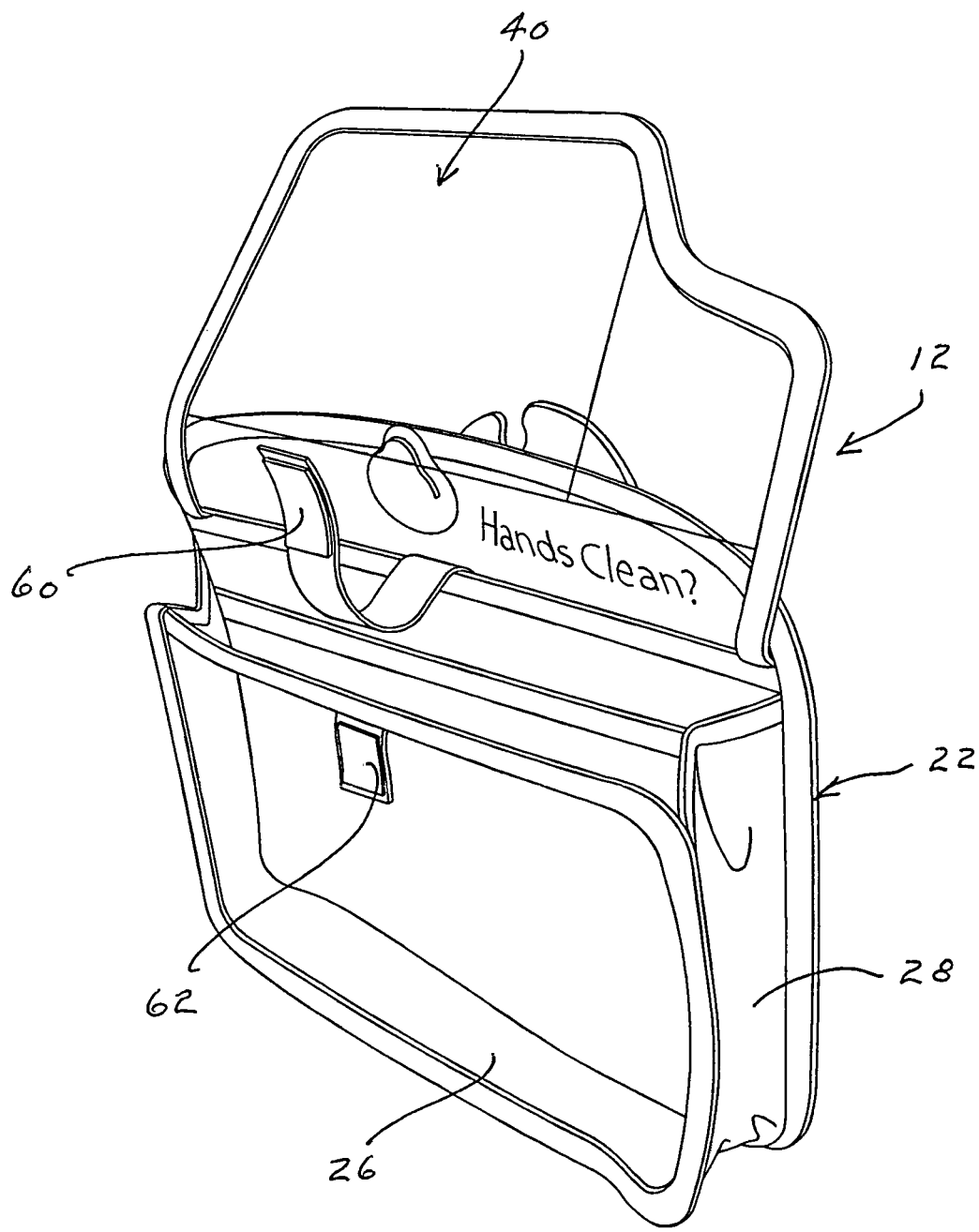
FIG. 3 is a view similar to that of FIGS. 1 and 2 with the front flap of the container in a raised position.

A front flap 40 having a front surface 42 as well as peripheral edges 44 and an upper edge 46 is connected to the top panel 24 such that the flap 40 overlies a major portion of the front panel 26 in a closed or downwardly extending position as shown in FIG. 3 to access the storage spaces 32 and 34 via the open tops 33 and 35 respectively thereof.

The front flap as well as all the panels are preferably formed of non-porous plastic sheet material, e.g., vinyl resin, that is flexible and can easily be wiped clean and sanitized such as with anti-bacterial solutions. This is particularly important for the front flap 40 since the front flap 40 is the main barrier preventing germs from entering the interior portions of the container 12. The edges of the front flap 40 as well as the panels may be fused for strength or alternatively provided with a narrow strip 50 of woven or braided material, e.g., nylon, polypropylene, etc., commonly referred to as binding having finished or selvage edges running the binding's entire length that is folded over the peripheral raw or unfinished edges to encase the edges and sewn in place as shown in the drawing. A locking strip 54 also formed of such woven or braided material and having an upper end 56 and a lower end 58 is attached to the top panel 24 and is adapted to be positioned over the open tops 33 and 35 of the storage spaces 32 and 34. A hook and loop fastener pair 60, 62 is attached to the rear surface of the strip 54 and to the front surface 36 of the front panel 26 to provide an easy and simple opening and closing system.

In addition, both the front panel 26 and the front flap 40 are preferably transparent whereas the back panel 22 and the intermediate panel 39, when provided, are preferably opaque. In this manner, items the patient desires to conceal from view can be placed in the storage space 35 while other items placed in the storage space 33 remain visible. In addition, the front flap 40 may include an open top pocket or pockets 66 formed by adding or incorporating a patch or patches 68 of sheet material attached to the inside surface thereof such as by fusion welding. In this way, a greeting, photograph, name tag, etc or informational pamphlet may be placed in such pocket and is clearly visible through the front surface of the front flap 40 to hospital personnel and visitors alike. For instance, a suitable greeting that could be placed in a pocket would be one that indicates the patient's preferred name. Also, the front of the top panel is also preferably provided with one or more messages, e.g., "Hands Clean?", so everyone including the patient is reminded of the need to prevent germs and sanitize by periodically wiping down at least the front surface of the front flap 40 as well as hand sanitizing the patient's and visitors' hands.

Figure 5:
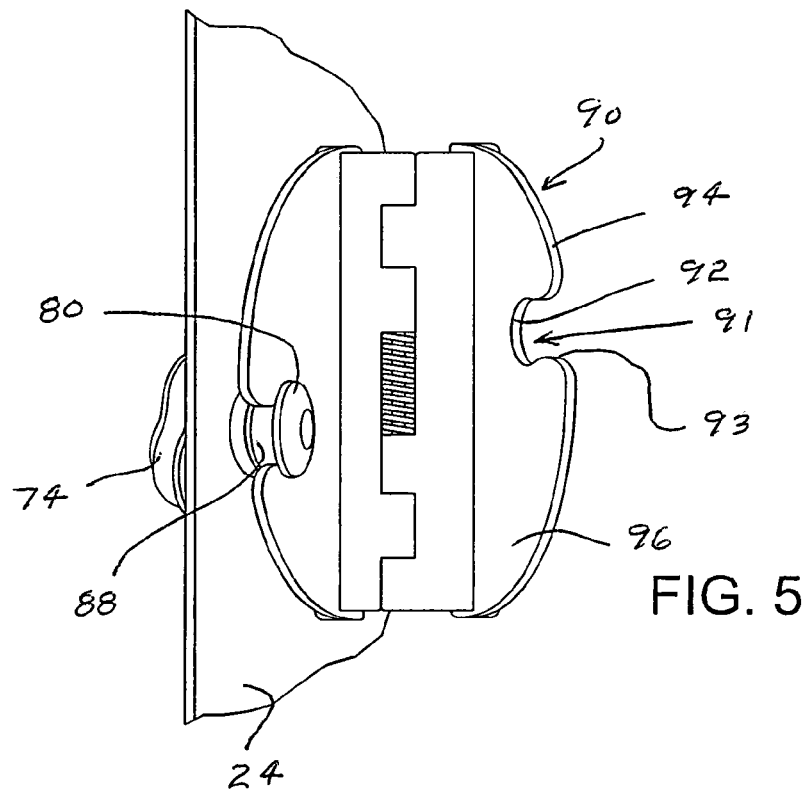
FIG. 5 is a top plan view of FIG. 4 showing one container connected to the clamp.
Figure 6:
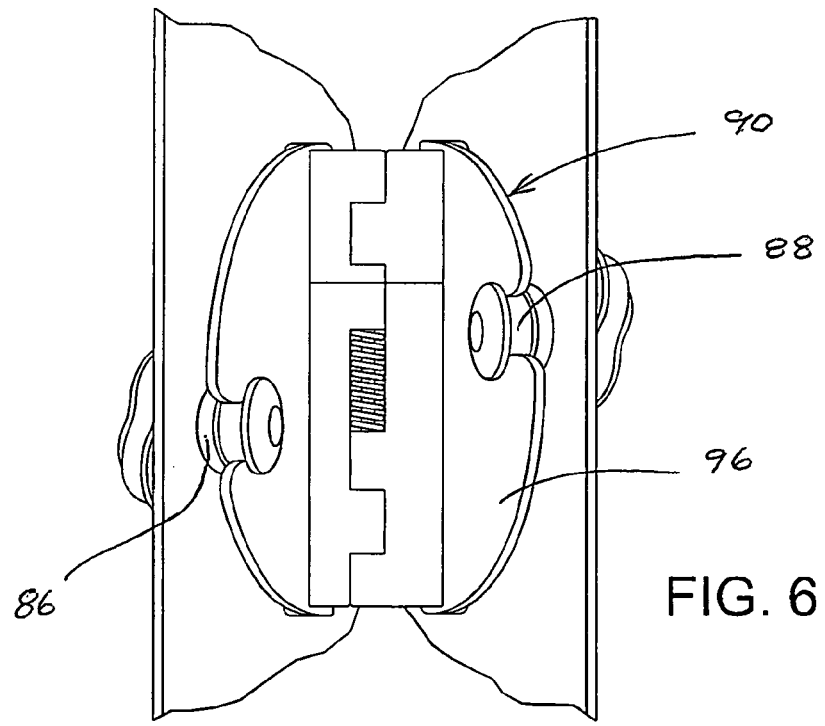
FIG. 6 is a top plan view of FIG. 4 showing two containers connected to the clamp.
Figure 7:
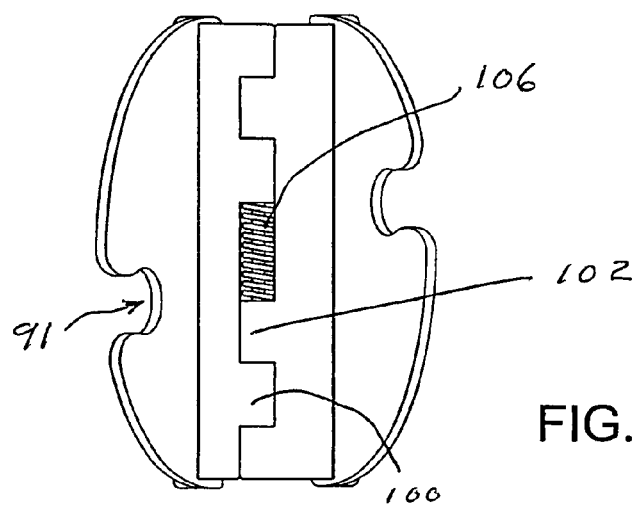
FIG. 7 is a top plan view of FIG. 4 with the container and the mounting system removed.
Figure 8:
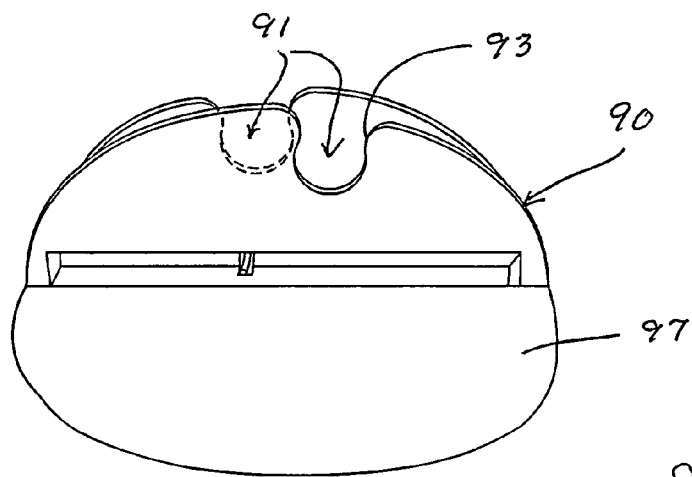
FIG. 8 is a left side elevational view of FIG. 7.
Figure 9:
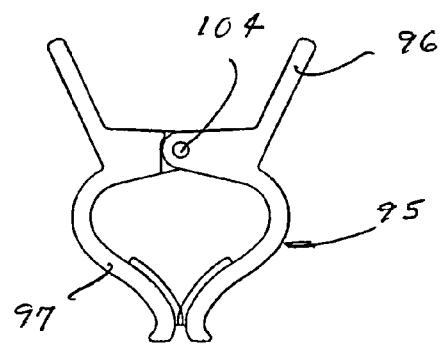
FIG. 9 is a front elevational view of FIG. 7.
Figure 10:
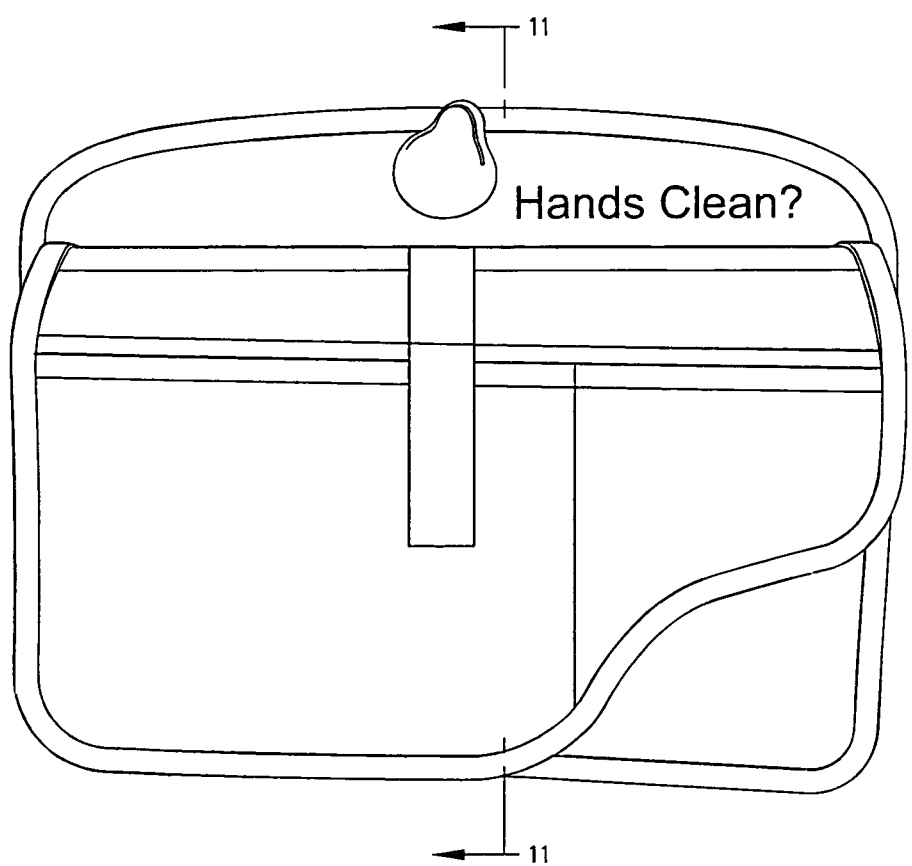
FIG. 10 is a front elevational view of FIG. 1.
Figure 11:
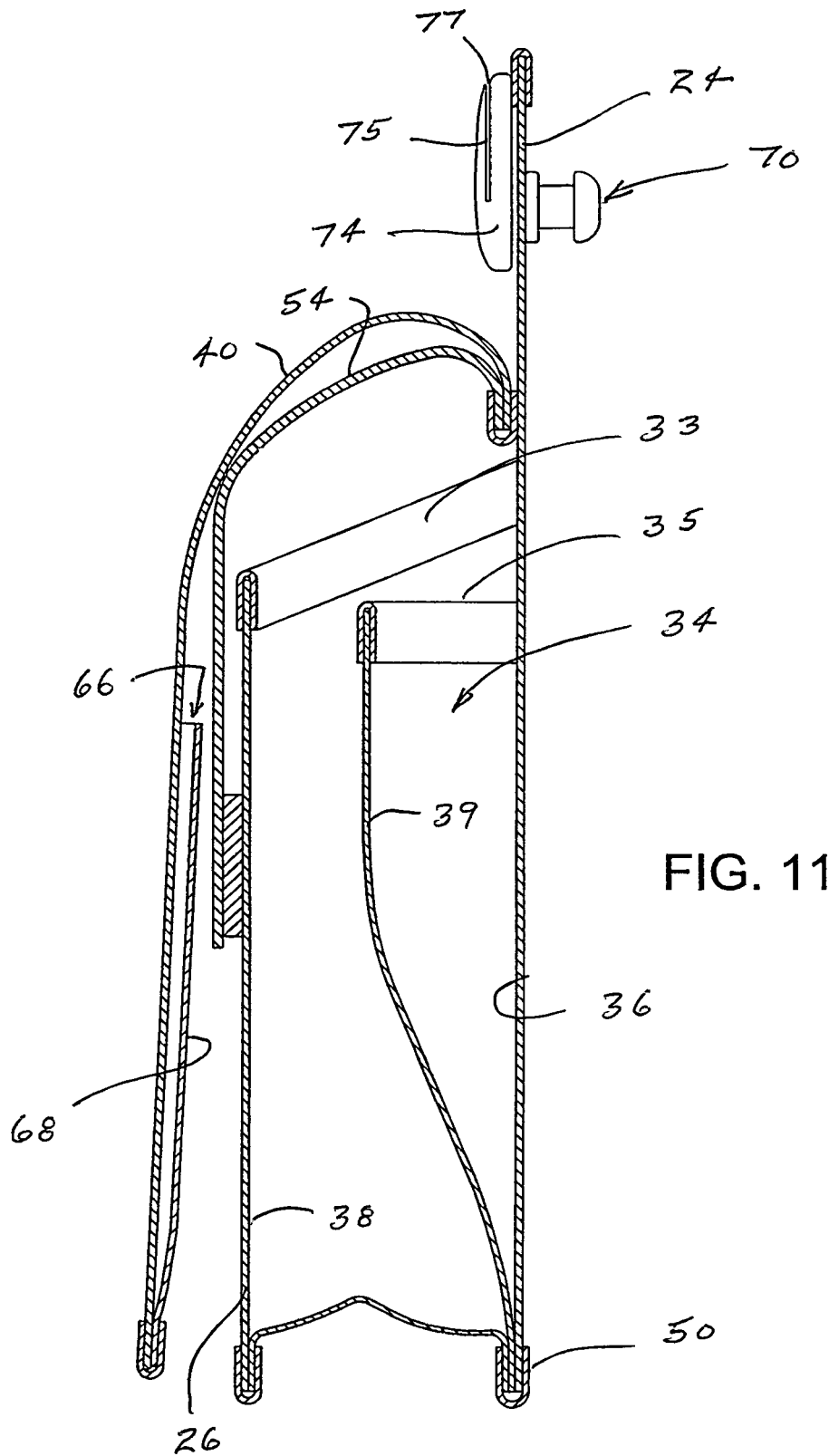
FIG. 11 is a cross-sectional view along the line 11-11 of FIG. 10.

The attachment means 18 by which the container 12 is mounted to a hospital related member, e.g., the bed side rail, includes a trunnion member 70 that is connected to a rigid portion 19 of the container 12 that provides a rounded bearing surface, e.g., in the embodiment shown in FIGS. 5-7, through the top panel 24 thereof and a clamping member 90 that, in turn, is connected to the trunnion member 70 at least in the area through which the trunnion 70 extends. In order to reinforce the top panel 24 and to add rigidity thereto, a rigid insert 25 of plastic and the like may be added generally by utilizing a double layer of sheet material to form the top panel and sandwiching the insert 25 therebetween. The trunnion member 70 includes an elongated shaft or plug 72 having an enlarged head or button 74. The plug 72 extends through an opening 27 in the top panel 24 and is provided with fastening means for attaching a connecting boss 80 to the terminal end 76 thereof. Such attaching means 18 may include a threaded channel 78 into which fastener 82, e.g., a screw or bolt, passing through a hollow bore 84 of the boss 80 serves to connect the plug 72 and boss 80 together after inserting the plug 72 into the bore 84 of the boss 80. The fastener 82 could alternatively be omitted and the plug 72 and boss "heat staked" together. The boss may include a flange 86 on the end proximal to the top panel 24 to apply pressure to the top panel, that is, the top panel 24 is, in effect, sandwiched between the rear face 75 of the button and the flange 86. The boss 80 includes a reduced diameter central pivot support surface 88 that, in turn, is received by a keyhole-shaped cutout 91 downwardly extending from the upper edge 94 of at least one of the opposed handles 96 of the clamp 90 to support the container 12 and defining a rounded bearing surface 92 in pivotal supporting relationship with the support surface 88 of the above-indicated trunnion connection.

Figure 5A:
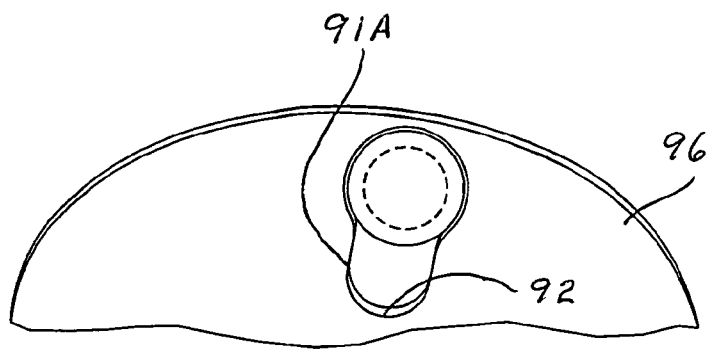
FIG. 5A is a partial elevational view of an alternate trunnion mounting means.
Figure 5B:
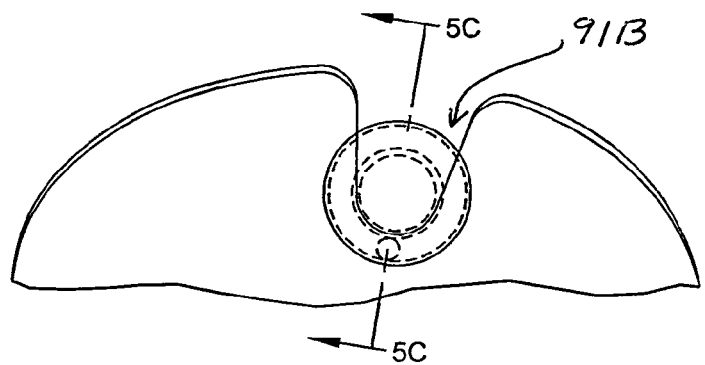
FIG. 5B is a partial elevation view similar to FIG. 5A showing another trunnion mounting means.
Figure 5C:
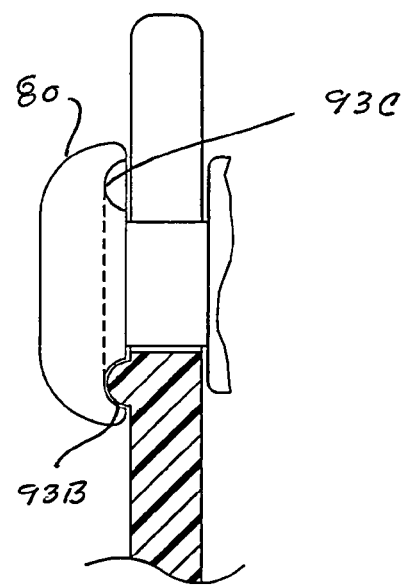
FIG. 5C is a sectional view along the line 5C-5C of FIG. 5B.

It should be pointed out that other ways of forming the rounded bearing surface 92 in the clamp handles 96 can be utilized (see FIGS. 5A and 5B). In FIG. 5A, the opening is not formed by a downwardly extending cutout 91 but passes through the body of the handle and is in the shape of a keyhole opening 91A wherein the lower reduced diameter portion thereof forms the rounded bearing surface 92, and the enlarged portion enables an already assembled trunnion member 70 to extend laterally therethrough for positioning of the pivot support surface 88 thereof thereon. Additionally, as shown in FIG. 5B and FIG. 5C, while the opening is formed by a downwardly extending cutout 91B, such cutout does not include a reduced diameter entrance as a means to retain the trunnion to the handle but alternatively utilizes an outwardly extending detent 93B which extends (as by snap fit) an arcuate recess 93C formed on the inside surface of the boss 80. Thus, the bearing surface 92 and the trunnion support surface 88 interaction enables the free-swinging suspension of the container with respect to the docking base to remain the same as above explained with reference to the embodiments shown in FIGS. 5-9 and FIG. 5A. Thus, the term "cutout" as utilized herein is intended to cover the various cutout forms disclosed above, e.g., cutouts 91, 91A and 91B.

Figure 4:
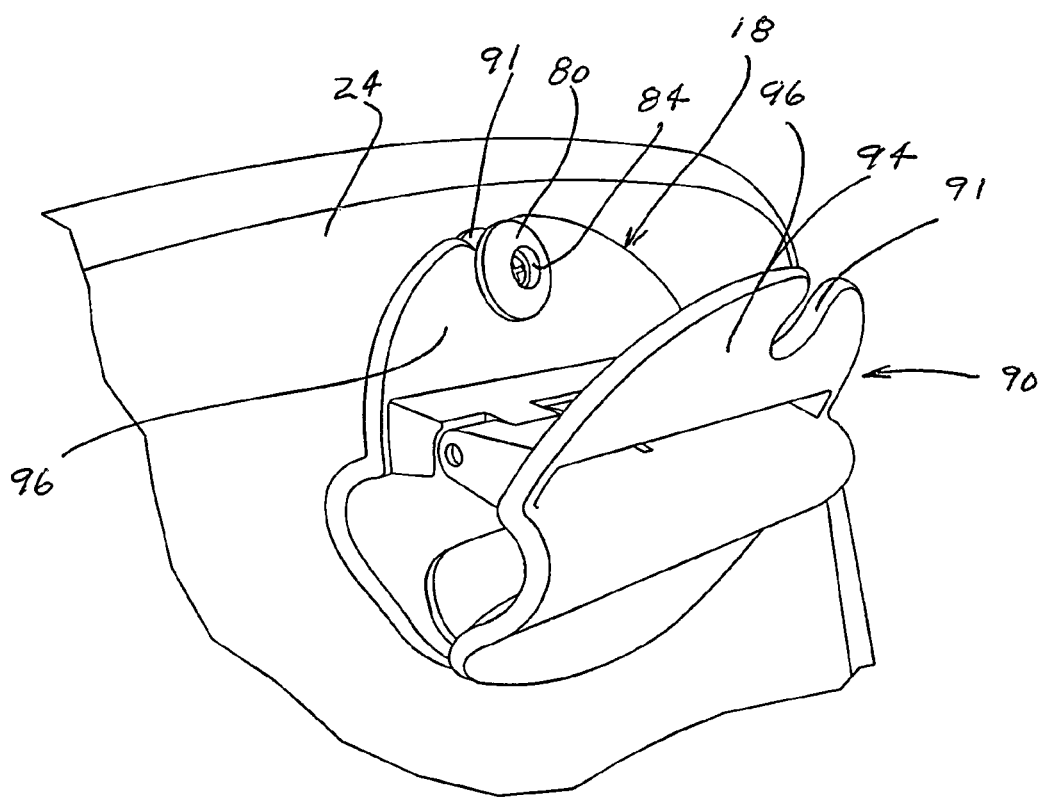
FIG. 4 is a partial rear perspective view of FIG. 1 showing the clamp utilized to connect the container to a hospital related member such as the side rail of a hospital bed as well as a portion of the system of mounting the container to such clamp.
Figure 4A:
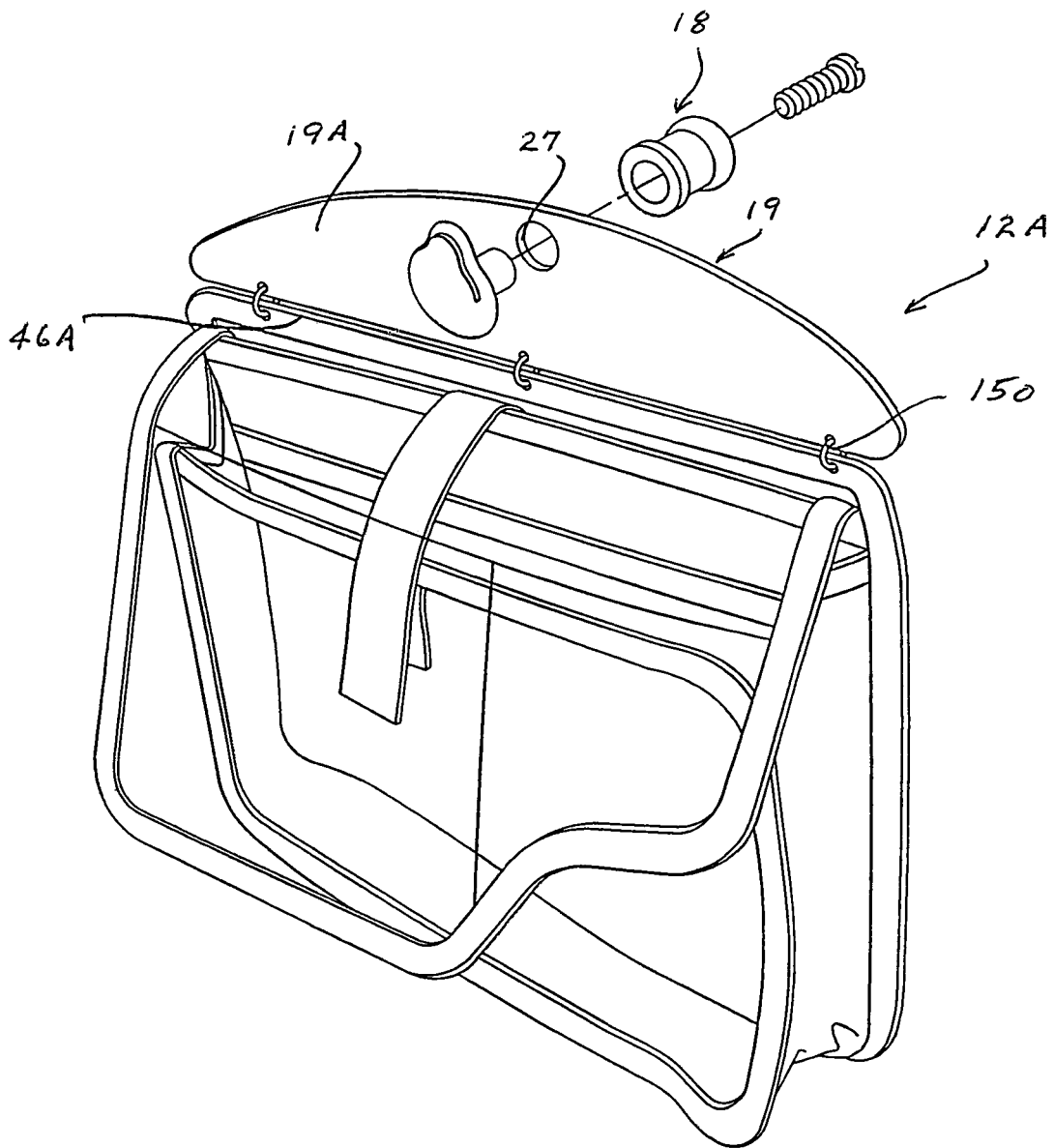
FIG. 4A is a front perspective view of a modified container form.
Figure 4B:
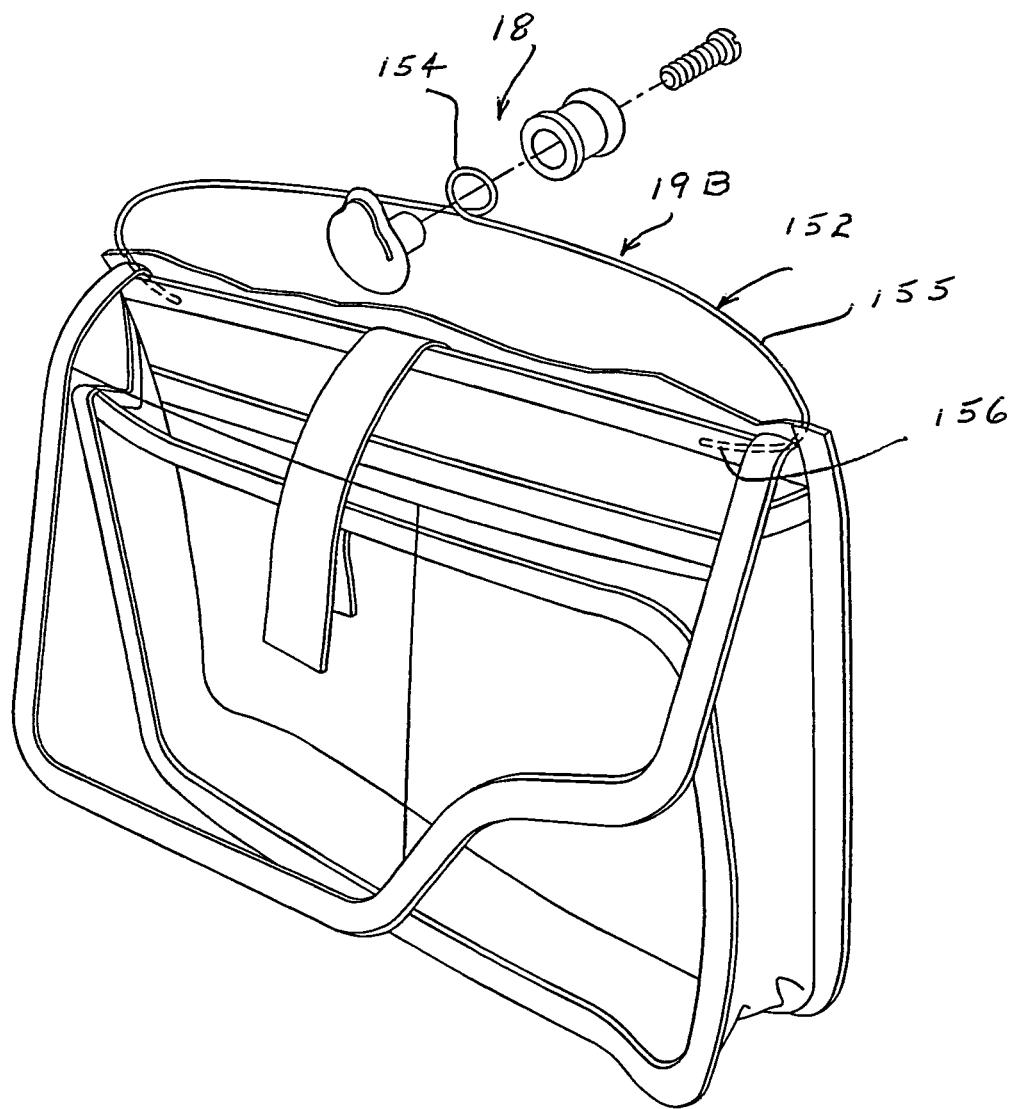
FIG. 4B is a front perspective view of another modified container form.

It should also be pointed out that the rigid portion of the container which interacts with the trunnion member to provide the desired pivotal mounting of the container to the docking base and thus to the hospital related member can be formed by alternate constructions such as those shown in FIGS. 4A and 4B. Such rigid portion 19 in part shown in FIG. 4 and as further explained with reference to FIG. 12 is formed by the area surrounding hole 27 through the top panel 24 but as above referred to can take other forms. One such alternate form of a rigid portion 19A is shown in FIG. 4A wherein the top panel, although configured similar to that of FIG. 4, utilizes a rigid panel which instead of being, in effect, a continuation of the back panel is a separate member having a lower edge that is attached to the upper edge 46A of the container 12A via fasteners 150. Another form of an alternate rigid portion 19B is depicted in FIG. 4B wherein a rigid wire 152 that is bent upon itself to form an integral rigid circular opening 154 centrally thereof which, in effect, forms the rigid portion 19B through which portions of the trunnion member 70 may be inserted as with the previously described embodiments. The wire includes a central body 155 and opposed ends 156 which may be inwardly bent such that those ends can be inserted into the selvage when present in the upper edge of the container or melt embedded into such upper edges as when formed from plastic trim such that the wire 152 and the remaining portions of the container are connected to each other.

Figure 12A:
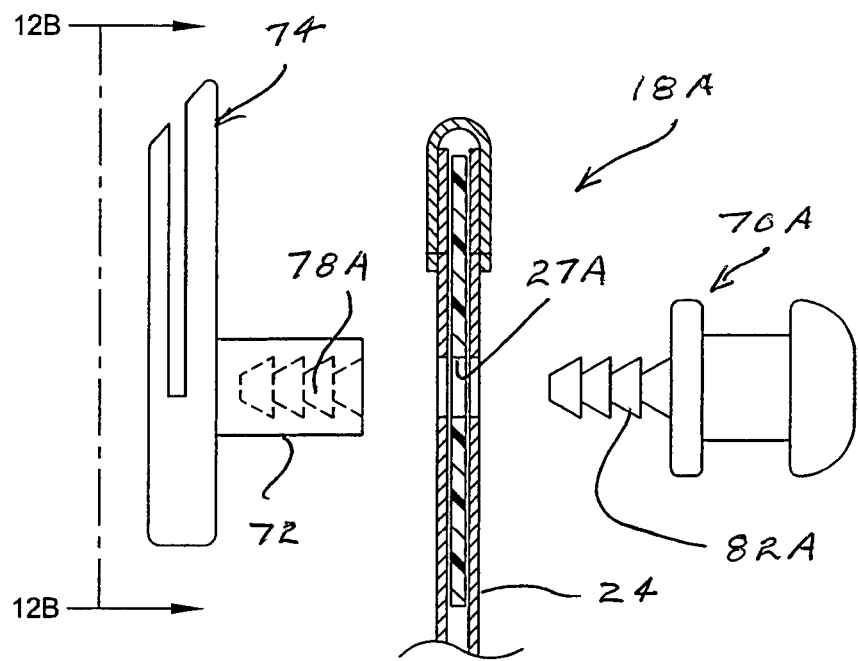
FIG. 12A is a view similar to FIG. 12 showing an alternate attachment means.

Referring now to FIG. 12A, a modified form 18A of the attachment means is shown whereby a trunnion member 70A may be attached to the rigid portion of the container, e.g., the top panel 24, thereof. Instead of utilizing a separate bolt or screw 82, such modified trunnion member 70A incorporates such threaded screw or bolt 82A into the boss 80A whereby the bolt 82A passes through a smaller opening 27A for connection with the plug 72 via internal threads 78A therein.

The clamp 90 includes opposed elongated members 95 connected together at central portions thereof and defining the handles 96 at the upper portions thereof and opposed jaws 97 at the lower portions thereof. The central connection of the members 95 is formed by interlocking lugs 100 and 102 extending inwardly from the opposed handles 96 through which a hinge pin 104 and spring 106 serves to interconnect the opposed handles such that they are biased to an open longitudinally outwardly angled position and when the handles 96 are forced towards each other such as by a grasping motion serve to open the normally closed jaws 97. In this way, the clamp 90 can be securely fastened but easily removed from a hospital related member, e.g., a bed rail, crutches, chair, table, a tubular portion of a walker, an IV pole or wheel chair arm. Upon release of the handles 96 from their proximal jaw opening position, the handles 96 assume a more upright and vertical position dependent upon the width or diameter of the member grasped by the jaws 97. An advantage of structuring the cutouts 91 at the upper edges 94 of the handles is that this position assumes that the trunnion member 70 and thus the pivotal connection between the container 12 and the clamp 90 is vertically spaced above the jaws and through the connection of such jaws with the hospital related member above such member. This positioning, in effect, lifts the containers considerably above the hospital related member and in some cases such as with connection to hospital bed rails serves to prevent the containers from resting in an inconvenient and relatively inaccessible position between the outer edge of the mattress and the bed rail. This positioning also assures maximum visibility to the front of the container. A detailed description of such a suitable spring clamp is shown in U.S. Patent Publication 2009/0019678 published Jan. 22, 2009, the disclosure of which is incorporated herein by specific reference thereto.

Preferably, each of the handles 96 includes a cutout 91 such that a pair of containers 12 can be mounted on the clamp 90 each with self-leveling, pivotal movement with respect to the clamp and thus, in turn, positioned on each side of the same hospital related member on which the clamp is mounted similar to saddle bags. The cutout 91 includes a narrowed entrance 93 of a diameter slightly less than that of the trunnion member pivot support surface 88 such that the boss 80 must be forced or snapped into the rounded bearing surface 92 of the cutout 91 such that the pivotal connection is purposely retained even when the hospital related member is angularly moved with respect to the supporting floor 20. As previously indicated, the alternate cutout forms described herein may be utilized as well, and such alternate forms would be interconnected with the trunnion in a manner dictated by their respective constructions. Also, by having one cutout 91 on each handle 96, one container 12 may be positioned facing outwardly towards the visitor, i.e., on the visitor's side, of a bed rail and another container 12 facing inwardly towards the patient, i.e., on the patient's side, of the bed rail thus better enabling the division of the patient's items between the two containers dependent upon the privacy or personal nature of the items, e.g., notices, reminders, name tags and sanitizing lotion or fluid on the public side and more personal items on the patient's side.

The above described embodiments assume an attachment means 18 that is separate from the docking base, e.g., the clamp 90, and then the trunnion means is attached thereto. However as shown in FIGS. 6A and 6B, a modified forms of the trunnion member means may be either attached to a portion of the docking base, e.g., the clamp 90A, prior to mounting the container thereto by conventional attachment means such as the fastener 82 as shown in FIG. 6A or may be integrally molded to the clamp 90B as shown in FIG. 6B.

Figure 6A:
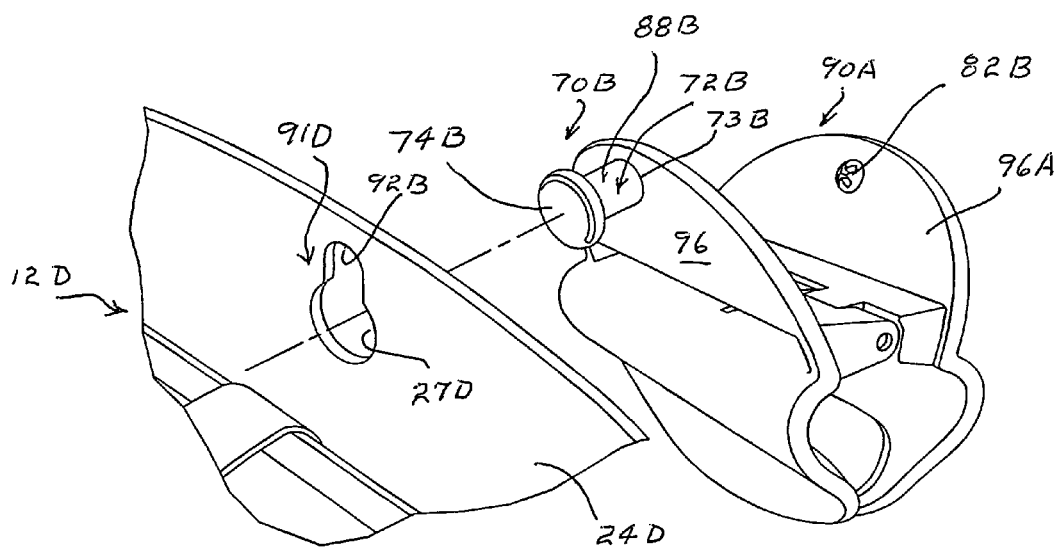
FIG. 6A is a view similar to FIG. 6 but showing a modified form of the invention wherein the attachment means is mounted to the docking base, e.g., the clamp.

Turning to FIG. 6A, trunnion member 70B includes an enlarged head or button 74B from which a shaft or plug 72B extends. Plug 72B includes an end wall or face 73B which abuts the surface of the handle 96A and is attached thereto by a screw or bolt 82B positioned on the opposite surface of the handle and passing through the handle body into the plug 72B which may be threaded to accommodate such attachment. With the trunnion member 70B so attached to at least one of the handles 96 and preferably both, the button 74B is adapted to pass through an enlarged opening 27D of cutout 91D formed in panel 24D of a modified container 12D. The cutout 91D is, of course, inverted as compared to cutout 91A since the modified attachment means is secured to the clamp as opposed to the container. Accordingly, the outer surface of the plug 74B serves to form a pivot support surface 88B which contacts the rounded bearing surface 92B formed at the reduced diameter upper portion of the keyhole shaped opening 27D which defines the cutout 91D. This pivotal mounting allows the container to pivot freely with respect to the clamp 90A as in the previous embodiments.

Figure 6B:
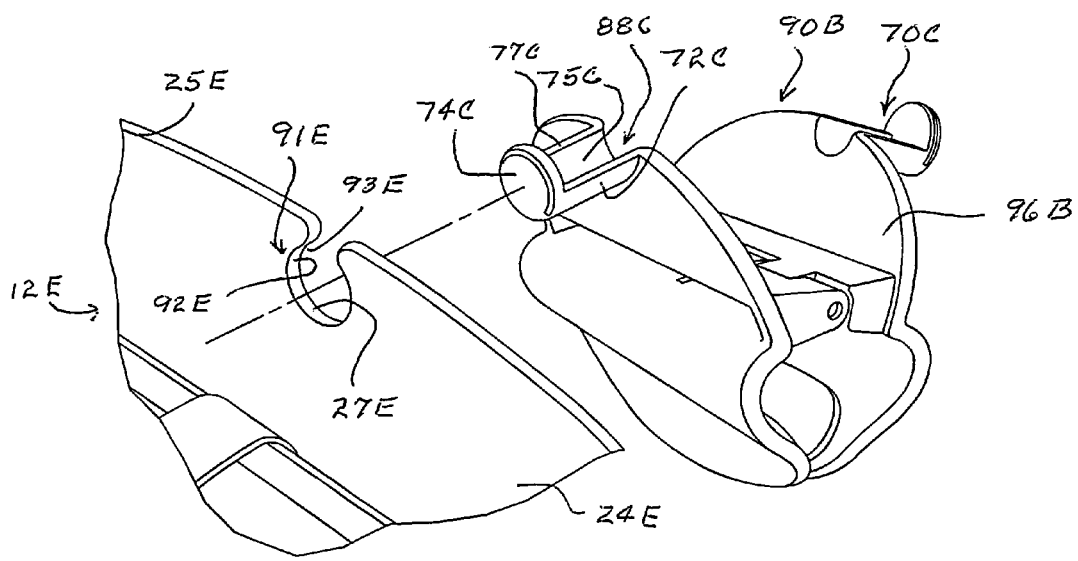
FIG. 6B is a view similar to FIG. 6A but showing another modification thereof.

Turning to FIG. 6B, a still further embodiment is shown where a trunnion member 70C is integrally formed with the handle(s) 96B as by injection molding. Such trunnion member includes a shaft or plug 72C outwardly extending from the outwardly facing face of at least one and preferably both of the handles 96B of clamp 90B. The plug 72C terminates in an enlarged head or button 74C which is adapted to pass through the enlarged portion of the opening 27D as described with reference to the FIG. 6A embodiment. The plug 72C includes a hollow body defined in part by the truncated walls 75C which, in turn, define longitudinally extending surfaces 77C which serves to form a pivot support surface 88C which, in turn, is adapted to contact the rounded bearing surface 92B of the cutout 91D. The free pivoting relationship between the clamp and container is achieved as with the previously described embodiments. The surface 77C may be rounded in cross section so as to enhance such pivotable motion.

It should be noted that with the above described embodiments of FIGS. 6A and 6B that a modified form of cutout 91E may be formed in the upper panel 24E of a modified form of container 12E. Such cutout 91E is similar in form to cutout 91 but downwardly extends from the upper edge surface 25E of the panel 24E as opposed to downwardly extending from the edge 94 of clamp 90. The reduced diameter lead in portion 93E of cutout 91E adjacent the enlarged opening 27E forms rounded bearing surface 92E that facilitates the desired free pivotal motion between the container 12E and the clamp 90A or 90B. Stated differently, the trunnion members 70B and 70C can be utilized in conjunction with either cutout 91D or 91E.

Figure 13A:
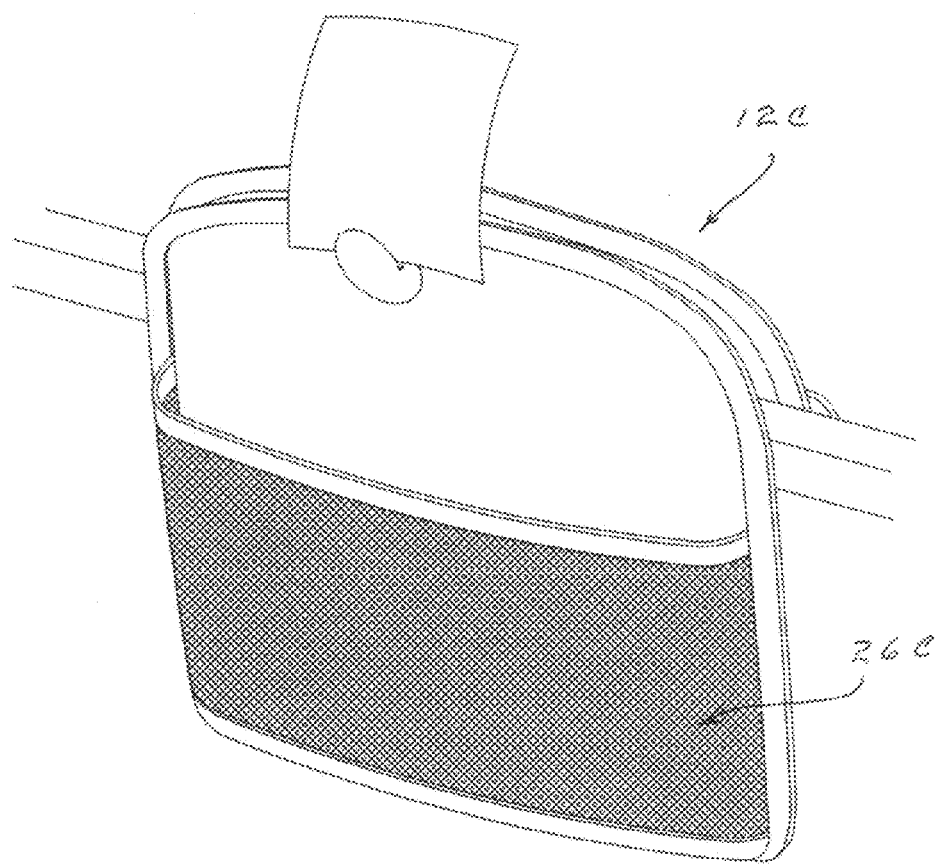
FIG. 13A is an enlarged partial view similar to FIG. 13 but illustrating an alternate outside container configuration.

With further regard to the division between the public and private (hospital vs. patient) sides of the bed or other hospital related member to which the container is mounted, it should be pointed out that a simplified version of the container can be utilized for mounting on the public side. An example of such a simplified container 12C is shown in FIG. 13A. Therein, the container 12C omits the front flap of the container 12 since the sanitation and privacy features of such flap are unnecessary on the public side and provides a front panel 26C preferably formed of mesh fabric and attached to the back panel 22 at the sides and bottom thereof. The pouch created by such panel 26C can be used by hospital staff for insertion of meal plans, notes from hospital staff, discharge papers and reading material, etc.

Figure 12B:
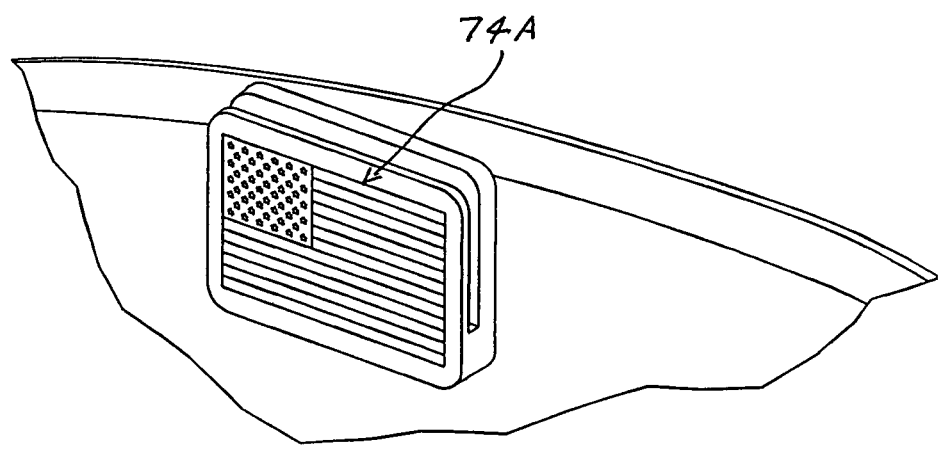
FIG. 12B is a perspective view of a portion of the container shown in FIGS. 12 and 12A wherein the button or clip is configured in a different shape.

With regard to notices and the like, the button 74 is provided with a narrow width slot 75 downwardly extending from the upper peripheral edge 77 thereof for the placement of a thin paper or cardboard sheet upon which time urgent or other related messages may be posted in a highly visible position by staff and/or visitors. The button 74 thus forms a message clip—the shape of which may be varied dependent upon the nature of the hospital facility, etc. For instance, the clip may take the form of the facility's logo or may be shaped to express various themes such as the American flag form of button 74A shown in FIG. 12B.

Figure 16:
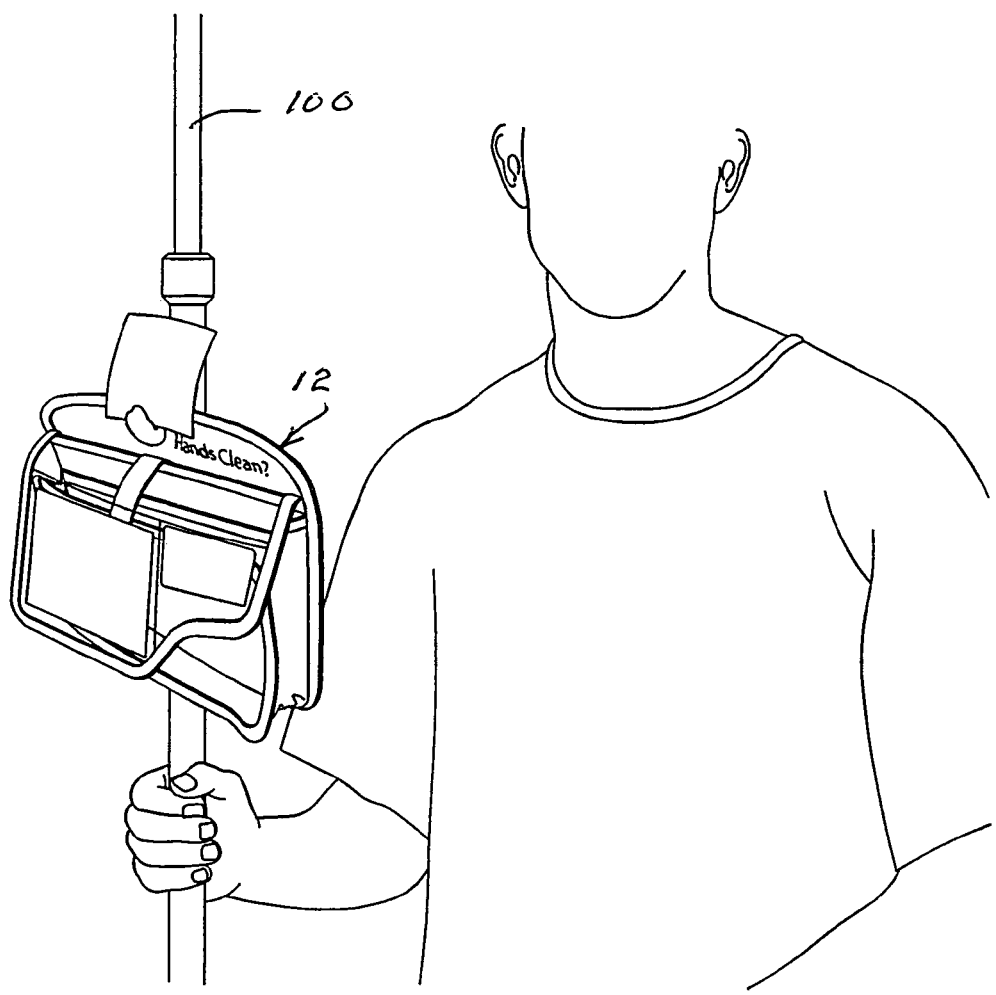
FIG. 16 is a perspective view of the container system of the present invention connected to an IV pole and held by a patient.
Figure 17:
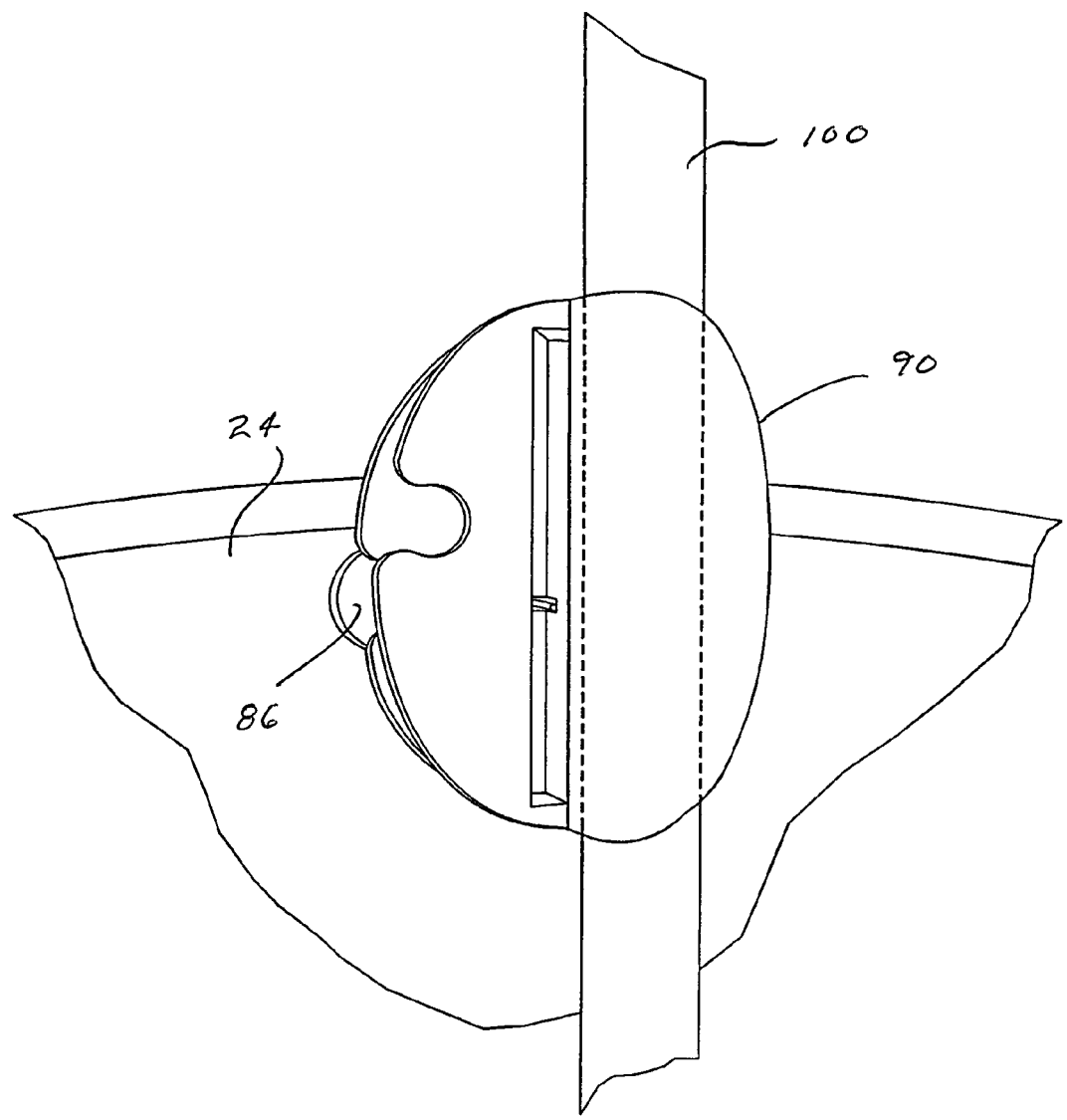
FIG. 17 is a partial rear perspective view of FIG. 16 showing how the container assumes a horizontal position even though the attachment clamp is disposed in a vertical attitude.

To illustrate how the clamp 90 or the modified forms 90A and 90B thereof may be mounted to hospital related members other than a bed rail, reference is made to FIGS. 16 and 17. In FIGS. 16 and 17, a container 12 is shown mounted via a clamp 90 to a vertically oriented IV pole 100. The clamp 90 assumes a vertical orientation as seen in FIG. 17 while the attachment means 18 enables the container 12 to remain horizontal as shown by the flange 86 positioned against the inside surface of the top panel 24 indicative of the central pivot support surface positioned in the bearing surface 92 of the cutout 91 proximal to the top panel. A similar arrangement of the above-described components takes place in different angular positions depending on the structure (hospital related member) to which the clamp 90 is mounted including walkers, wheel chairs and even conventional chairs, etc. as previously indicated.

Figure 14A:
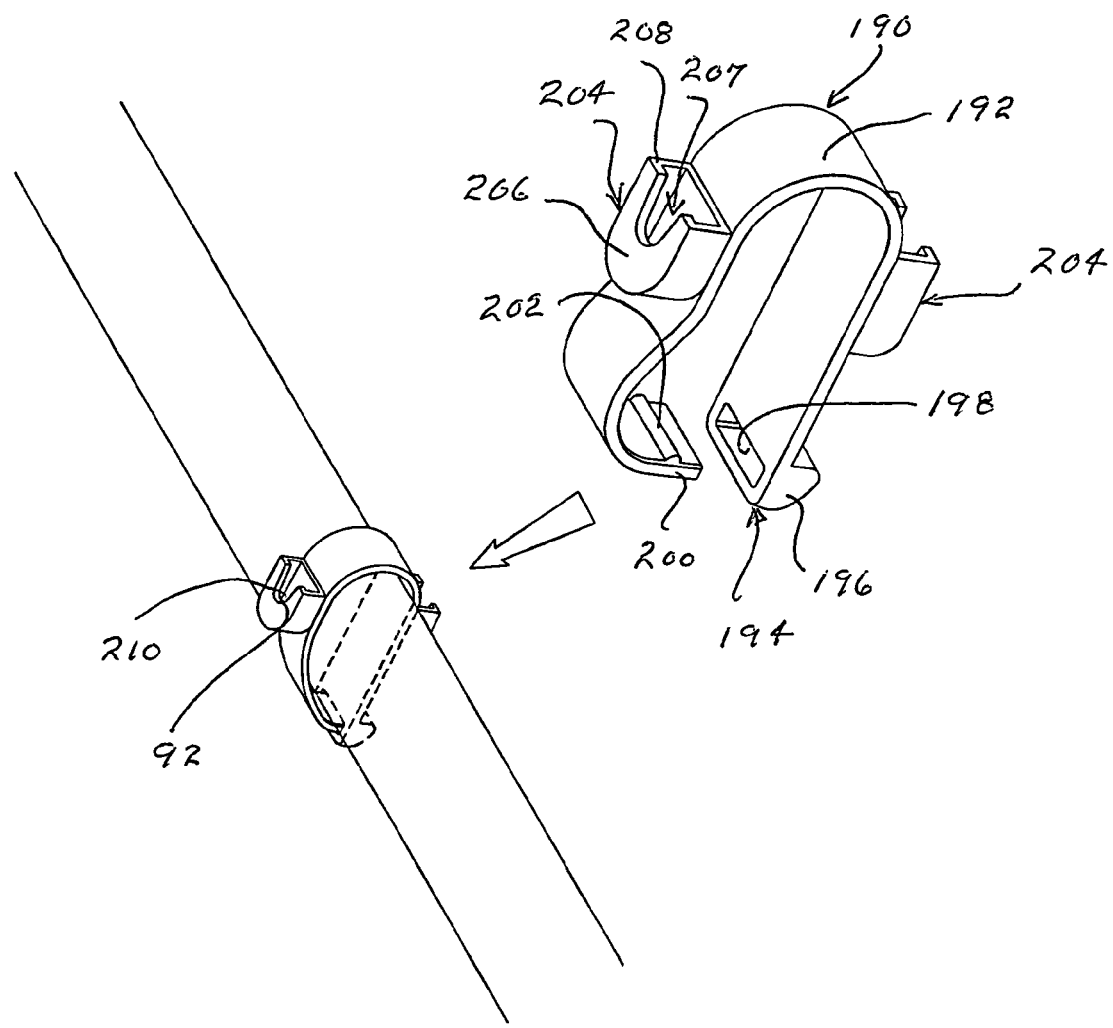
FIG. 14A is a perspective view showing an alternate means for attaching a container to a hospital related member.
Figure 15:
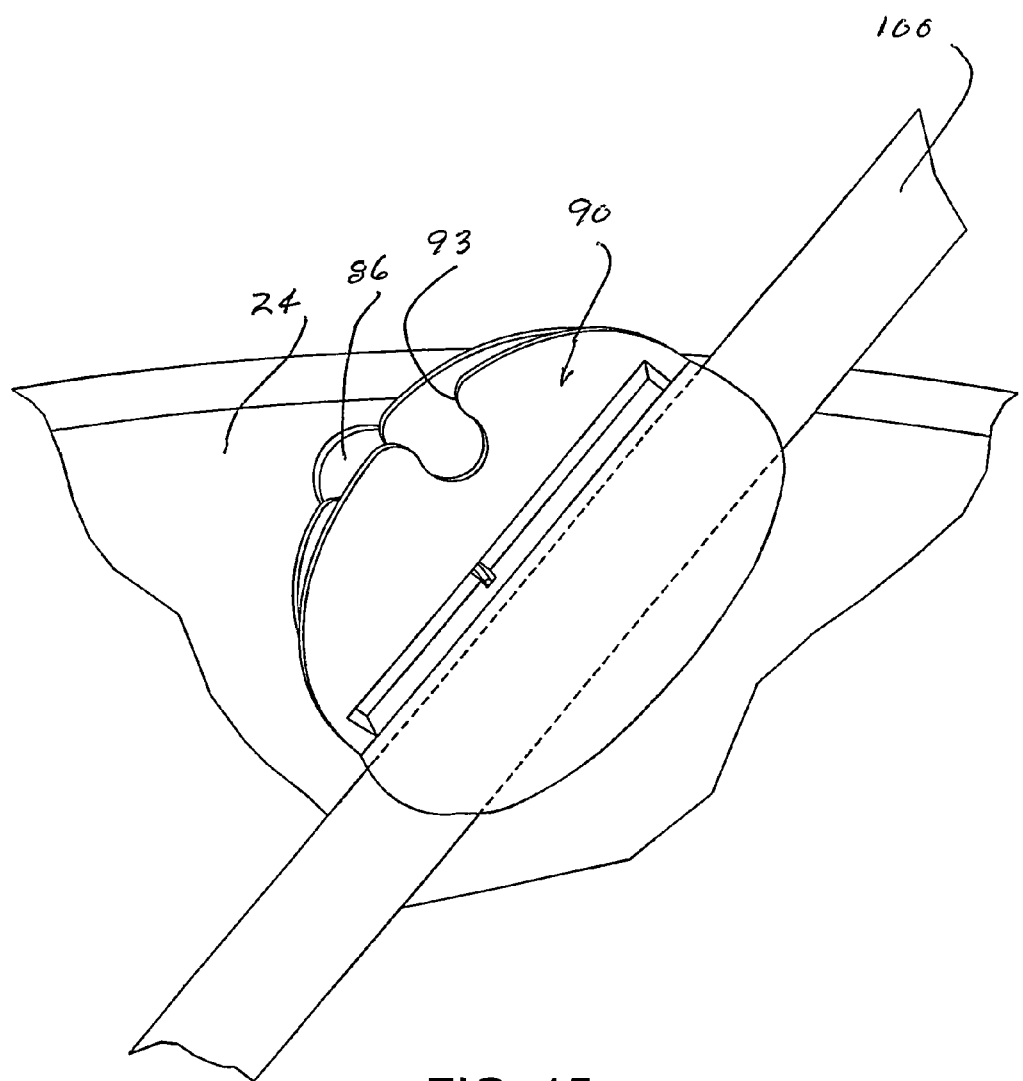
FIG. 15 is an enlarged partial perspective view of the clamp attachment system shown in FIG. 14 to illustrate the angular elevation of the clamp while the container remains level.

In the foregoing description of the invention in its various forms, the construction and function of the docking base has been illustrated with specific reference to the clamp 90. However, as previously pointed out, the docking base may also take forms different from such clamp. For instance with reference to FIG. 14A, one such modified or alternate construction of the docking base is depicted. Therein, a band 190 preferably formed of a somewhat stiff plastic is adapted to encircle the hospital related member. The band includes a central body 192 and opposite ends. One of the ends 194 terminates in a housing 196 including an open slot 198 for receipt of the other end 200. Such other end 200 includes an upstanding ridge 202 which when forced, e.g., snap fitted, into the slot 198 provides the means by which the band is attached to the hospital related member.

The body of the band includes at least one and preferably two hanger members 204 formed on opposed sides thereof. The hanger members include an outer wall 206 laterally spaced from the band body 192 to form a space 207 therebehind. The walls 206 include an upper edge 208 and a cutout 210 downwardly extending therefrom. The cutout 210 provides a rounded bearing surface 92 at the base thereof and thus along with the space 207 provides the means by which the trunnion member 70 may be positioned therein and function in the same manner as previously described to enable one or two containers to be positioned therein and function so as to enable the desired pivotal movement of the container with respect to the hospital related member. While the cutout 210 is depicted as in the form of cutout 91B previously described with reference to FIGS. 5B and 5C, the cutout or opening 210 could also take the forms depicted and described with reference to FIGS. 5 and 5A of the drawings as well as to the modified forms described in FIGS. 6A and 6B.

Figure 17A:
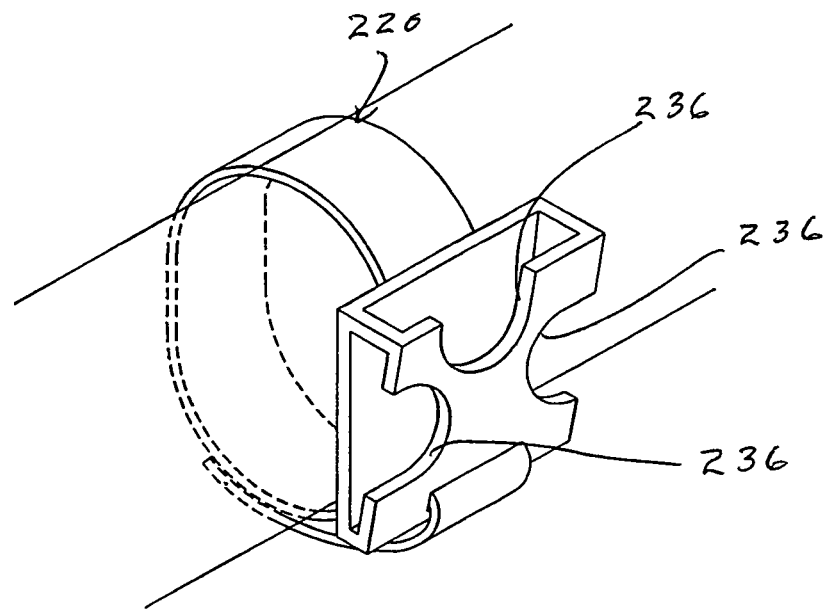
FIG. 17A is a partial perspective view similar to FIG. 14A showing a still further alternate means for attaching a container to a hospital related member, e.g. a pole.
Figure 17B:
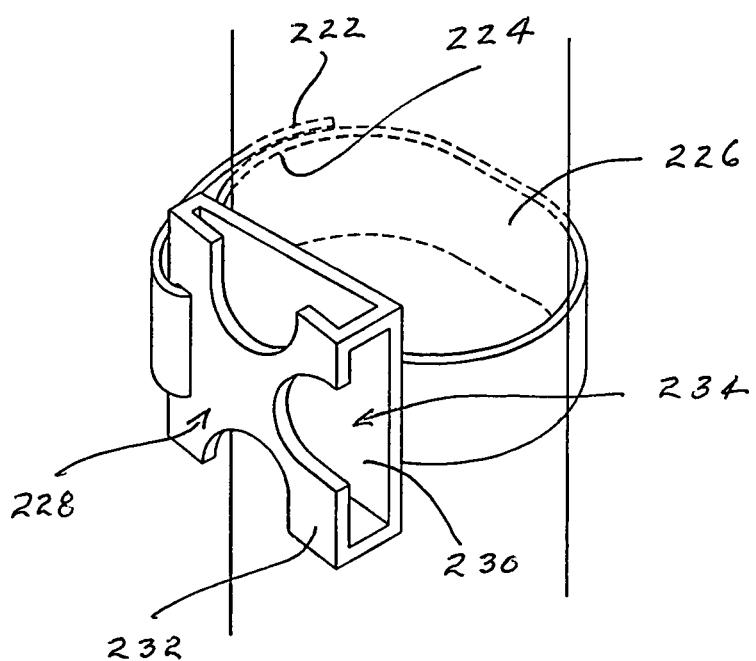
FIG. 17B is a partial perspective view showing the attachment means of FIG. 17A positioned in an alternate position.

A still further modified docking base form is shown in FIGS. 17A and 17B and has particular utility when used in transition as between a bed and a chair and when less permanent fastening of the docking base is desired. Therein, a band 220 preferably formed of a flexible plastic or strong woven material is adapted to encircle the hospital related member. The ends 222, 224 respectively are provided with loop and hook fastening means (Velcro) such that the band 220 can be easily fixed in position and removed. The central body 226 of the band includes a hanger member 228 having, in turn, an inner wall 230 attached to the band and an outwardly spaced outer wall 232 to form space 234 therebetween. The outer wall has a regular geometric peripheral edge, e.g., a square, and includes at least one and preferably three cutouts 236 inwardly extending from the edges thereof. Generally, the outer wall 232 is square or rectangular such that when these cutouts are utilized, the docking base will present a cutout in position to receive the trunnion member in several different directions. As with the explanation with reference to the FIG. 14A docking base embodiment, the cutouts 236 may also take the form of the various configurations set out in FIGS. 5, 5A and 5B.

Figure 18:
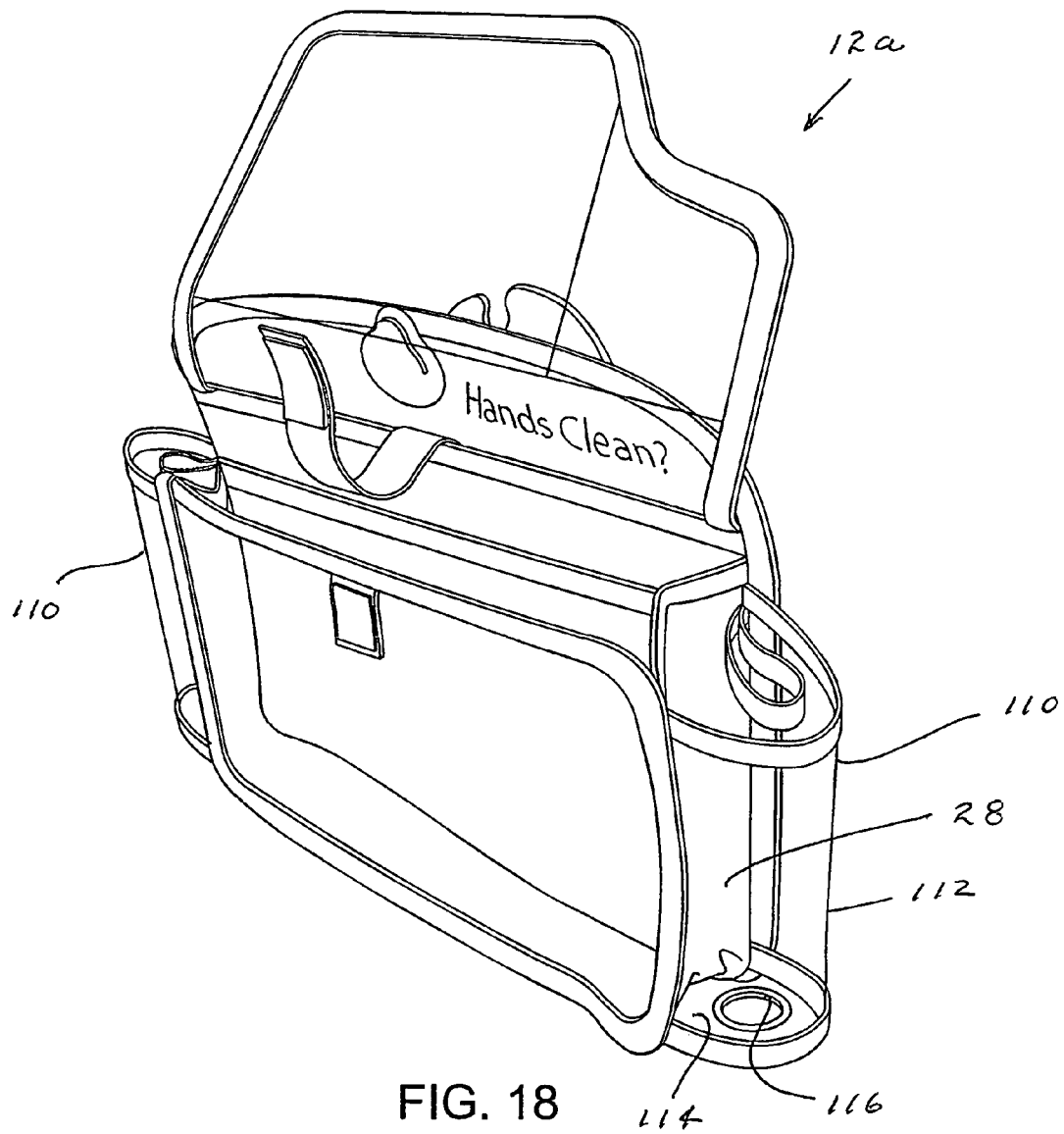
FIG. 18 is a partial perspective view similar to FIG. 3 but showing an alternate construction of the container.
Figure 18A:
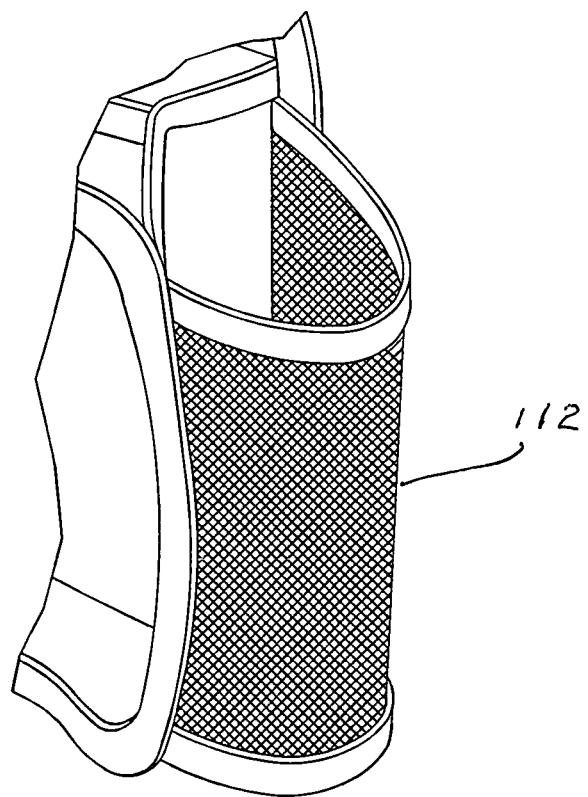
FIG. 18A is a view similar to FIG. 18 showing another embodiment.
Figure 19:
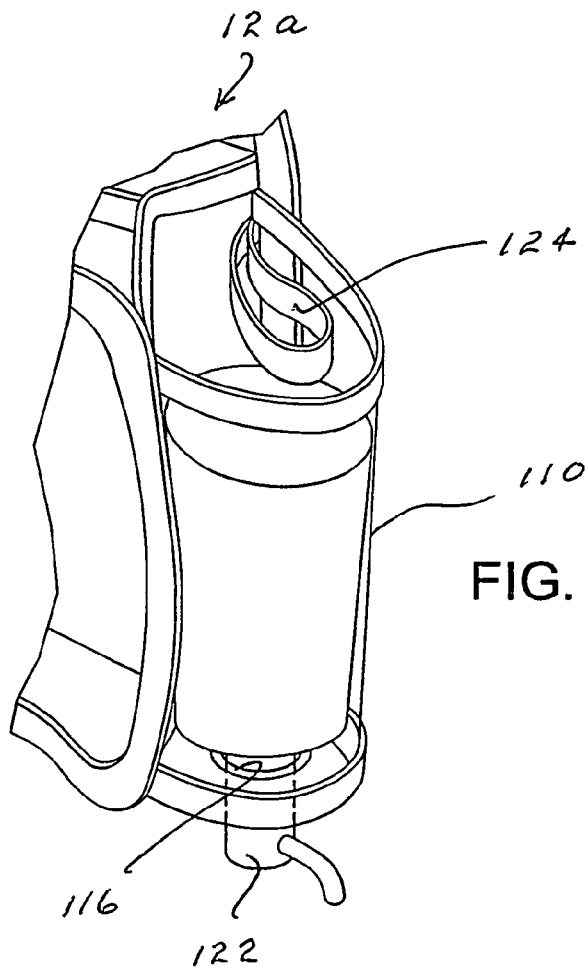
FIG. 19 is a partial view of FIG. 18 showing how a container of hand disinfectant can be positioned in one of the container side pockets shown in FIG. 18.
Figure 19A:
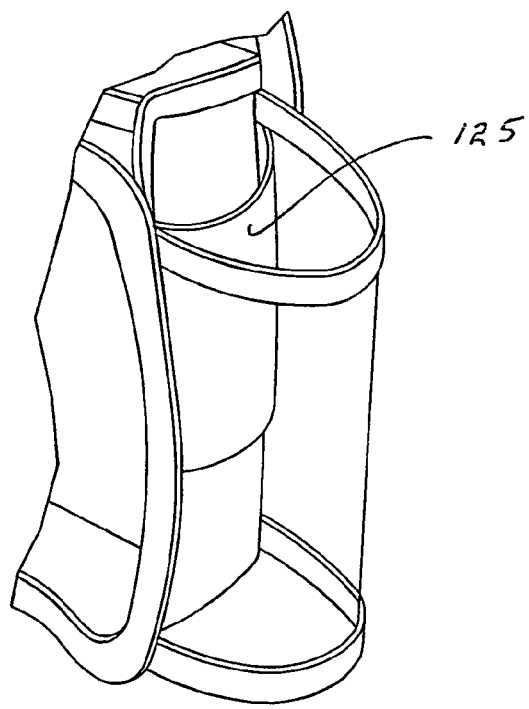
FIG. 19A is a view similar to FIG. 19 showing another embodiment.
Figure 20:
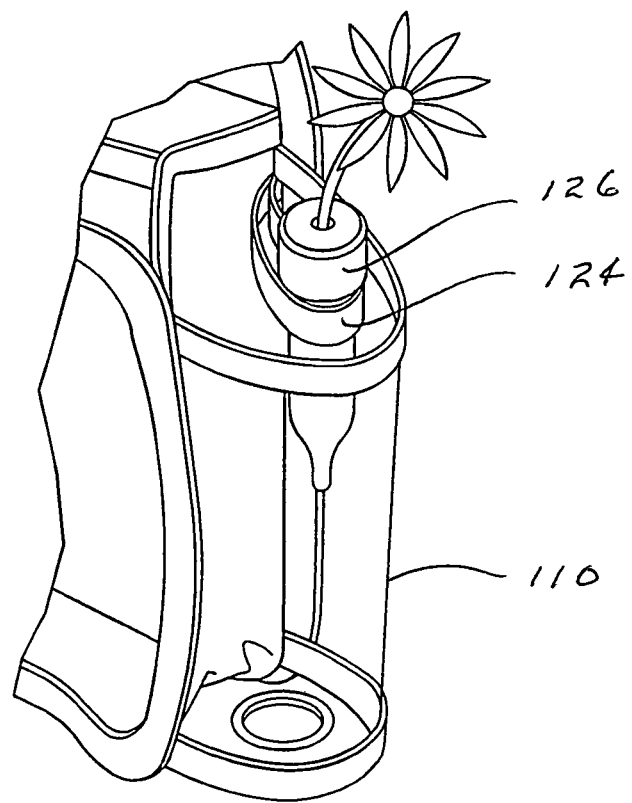
FIG. 20 is a partial view of FIG. 18 depicting a flower in a bud vase positioned in one of the container side pockets shown in FIG. 18.

Turning now to FIG. 18-20, a modified form of a container 12a is depicted wherein one or both side panels 28 are provided with a vertically oriented and laterally extending pocket 110. The pocket or pockets 110 include sidewalls 112 that may be rounded or rectangular and formed of transparent sheet plastic of the type forming the panels or of plastic or fabric mesh as depicted in FIG. 18a and further including a bottom wall 114 that, in turn, includes an opening 116 therethrough. The sidewalls 112 define a cavity 118 for receipt of a bottle 120 of antibacterial lotion that is preferably positioned in an inverted position therein such that the dispensing nozzle 122, e.g., a squirt-type cap or dispensing hand pump, thereof extends through the opening 116 to increase the ease of dispensing fluid onto one's hands. In addition, the pockets 110 may include a closed loop 124 preferably formed from web or other open mesh type material similar to that utilized in the binding portions of the panels. The loop 124 may be utilized to orient the dispensing nozzle 122 of a lotion, etc. bottle when such is oriented base end down in the pocket 110 or for supporting a bud vase 126 used for displaying a natural or artificial flower or other decorative object. Also as shown in FIG. 19A, the loop 124 may be omitted and a pouch or pocket 125 provided in addition to or as a replacement for such loop. As may be readily apparent, these pockets can be used to hold MP3 players, glasses and other items the user wants easily accessible.

While there is shown and described herein certain specific structure embodying this invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An organizing and storage system for patients in hospital and related medical facilities having a floor on which a hospital related member is supported comprising, a pouch-like container and means for attaching said container to a docking base in turn adapted for attachment to said hospital related member, said container having a rigid portion in turn supporting said means for attaching said container to said docking base, said container including a front panel and a back panel so as to form an interior storage space between the front of said back panel and the back of said front panel and accessible via a top opening, and said attachment means accommodating relative rotation between said attachment means and said docking base such that said container is rotatable to a horizontally parallel position with respect to said facility floor, said rigid portion having forward and rear areas and wherein said attachment means comprising a trunnion member attached to said rigid portion and outwardly extending from the rear area of said rigid portion, said trunnion member rotatably supported by said docking base, said back panel upwardly terminating in a relatively rigid top panel which in turn defines said rigid portion, said top panel supporting said means for attaching said container to said docking base, wherein said attachment means comprising a trunnion member attached to and outwardly extending from the back of said top panel, said docking base being a clamp, said clamp including spring urged adapted for fixedly removable connection to said hospital related member and a pair of longitudinally spaced handles connected to said jaws.

2. The system set forth in claim 1, wherein said handles include at least one opening extending therethrough and forming a rounded bearing surface for said trunnion member.

3. The system set forth in claim 2, wherein said handles include at least one open circular slot downwardly extending from the upper edge of said handle leading into said rounded bearing surface opening, said slot having a narrowed initial opening, said trunnion member including a circular boss for connection to said opening such that said container is rotatably connected to said clamp and free to assume said horizontal position irrespective of the relative position of said clamp.

4. The system set forth in claim 2, wherein each of said handles including one of said rounded bearing surface openings wherein said openings are laterally spaced from each other and a pair of said containers supported on opposite sides of said clamp.

5. The system set forth in claim 2, said opening extending through a portion of the handle as opposed to downwardly extending from the upper edge of the handle, said trunnion member including a circular boss for connection to said opening such that said container is rotatably connected to said clamp and free to assume said horizontal position irrespective of the relative position of said clamp.

6. The system set forth in claim 5, said opening being keyhole shaped.

7. The system set forth in claim 2, wherein said handles include at least one open circular slot downwardly extending from the upper edge of said handle, said slot leading into said rounded bearing surface opening, said trunnion member including a circular boss for connection to said opening such that said container is rotatably connected to said clamp and free to assume said horizontal position irrespective of the relative position of said clamp, and means for positioning said trunnion member in said opening.

8. The assembly of claim 1, said front and said back panels connected to each other at their respective bottom edges so as to form an open top closed bottom storage space therebetween and wherein said clamp jaws are disposed vertically above said container closed bottom.

9. The system of claim 8, said front flap formed of sheet plastic material.

10. A container and positioning assembly comprising a pouch-like container and a docking base, said container attached to said docking base and supported for pivotal motion with respect thereto, said container having a back panel upwardly terminating in a top panel having a rigid portion, said top panel supporting attachment means for attaching said container to said docking base, said attachment means including a trunnion member attached to and extending outwardly from the back of said top panel, said trunnion member rotatably supported by said docking base, and said container further including a front generally planar flap having a front face of easily wipeable material, said flap hingedly connected to said back panel above said top opening and normally positioned in a downward position overlapping major portions of said front panel so as to require lifting to access said storage space and provide a germ resistant cover to said container.

11. The assembly of claim 10, said docking base being a clamp, said clamp including spring urged opposed jaws adapted for fixedly removable connection to a fixed position member and a pair of longitudinally spaced handles connected to said jaws and extending vertically upwardly from said jaws, said handles include at least one open circular slot downwardly extending from the upper edge of said handles, said slots having a narrowed initial opening, said trunnion member including a circular boss for positioning in said slot such that said container is rotatably connected to said clamp and free to assume a horizontal position irrespective of the relative position of said clamp.

12. The system set forth in claim 11, wherein each of said handles including one of said slots wherein said slots are laterally spaced from each other and a pair of said containers supported on opposite sides of said clamp.

13. The assembly of claim 11, said container further including a front panel disposed parallel to said back panel and connected thereto at their respective bottom edges so as to form an open top closed bottom storage space therebetween, said clamp jaws disposed vertically above said container closed bottom.

14. The system of claim 10, said container including foldable side panels connecting said front and back panels.

15. The system of claim 10, said docking base comprising a band adapted to encircle the hospital related member for attachment thereto, said band including at least one hanger member including an outer wall spaced from said band, said outer wall including a rounded bearing surface adapted for receipt of said trunnion member.

16. The system of claim 15, said band having opposite sides and a hanger member positioned on each of said opposite side thereof, said band further including opposed ends having locking means by which said band is releasably fastened to said hospital related member.

17. The system of claim 15, said band having a single hanger member, said pocket outer wall having a regularly shaped peripheral edge, said edge in turn having a plurality of circumferentially spaced cutouts which cutouts include said rounded bearing surface so as to enable said trunnion member to be positioned in multiple orientation with respect to said band.

18. The system of claim 10, said container including a pair of side pockets formed from vertically oriented sidewalls connected to said side panels on each side of said container.

19. The system of claim 18, said side pockets including a bottom wall having, in turn, an opening therethrough.

20. The system of claim 18, said side pockets including a closed loop positioned at the top thereof.

21. An organizing and storage system for patients in hospital and related medical facilities having a floor on which a hospital related member is supported comprising, a pouch-like container and means for attaching said container to a docking base in turn adapted for attachment to said hospital related member, said container having a rigid portion in turn supporting said means for attaching said container to said docking base, said container including a front panel and a back panel so as to form an interior storage space between the front of said back panel and the back of said front panel and accessible via a top opening, and said attachment means accommodating relative rotation between said attachment means and said docking base such that said container is rotatable to a horizontally parallel position with respect to said facility floor, wherein said attachment means comprising a trunnion member attached to said docking base and outwardly extending therefrom, said rigid portion of said container rotatably supported by said trunnion, said back panel upwardly terminating in a relatively rigid top panel which in turn defines said rigid portion, wherein said docking base is a clamp, said clamp including spring urged opposed jaws adapted for fixedly removable connection to said hospital related member and a pair of longitudinally spaced handles connected to said jaws.

22. The system set forth in claim 21, wherein said handles include at least one opening extending therethrough and forming a rounded bearing surface for said trunnion member.

23. The system set forth in claim 22, wherein said handles include at least one open circular slot downwardly extending from the upper edge of said rigid portion of said top panel leading into said rounded bearing surface opening, said slot having a narrowed initial opening, said trunnion member including a circular boss for connection to said opening such that said container is rotatably connected to said clamp and free to assume said horizontal position irrespective of the relative position of said clamp.

\* \* \* \* \*